(12) United States Patent
Jones

(10) Patent No.: US 9,002,431 B2
(45) Date of Patent: Apr. 7, 2015

(54) GARMENT MRI ANTENNA ARRAY

(71) Applicant: Randall W. Jones, Omaha, NE (US)

(72) Inventor: Randall W. Jones, Omaha, NE (US)

(73) Assignee: ScanMed, LLC, Omaha, NE (US)

( * ) Notice: Subject to any disclaimer, the term of this patent is extended or adjusted under 35 U.S.C. 154(b) by 0 days.

(21) Appl. No.: 13/683,602

(22) Filed: Nov. 21, 2012

(65) Prior Publication Data

US 2013/0137969 A1    May 30, 2013

Related U.S. Application Data

(60) Provisional application No. 61/563,413, filed on Nov. 23, 2011.

(51) Int. Cl.
| | |
|---|---|
| *A61B 5/05* | (2006.01) |
| *A61B 5/055* | (2006.01) |
| *G01R 33/34* | (2006.01) |
| *G01R 33/3415* | (2006.01) |
| *G01R 33/36* | (2006.01) |

(52) U.S. Cl.
CPC .......... *A61B 5/055* (2013.01); *G01R 33/34007* (2013.01); *G01R 33/34084* (2013.01); *G01R 33/3415* (2013.01); *G01R 33/3657* (2013.01)

(58) Field of Classification Search
USPC ............. 600/410, 421, 422; 2/69, 92, 93, 102
See application file for complete search history.

(56) References Cited

U.S. PATENT DOCUMENTS

| | | | |
|---|---|---|---|
| 4,825,162 | A | 4/1989 | Roemer et al. |
| 5,430,378 | A | 7/1995 | Jones |
| 5,435,302 | A | 7/1995 | Lenkinski et al. |
| 5,548,218 | A | 8/1996 | Lu |
| 5,594,339 | A | 1/1997 | Henderson et al. |
| 5,666,055 | A | 9/1997 | Jones et al. |
| 6,084,411 | A | 7/2000 | Giaquinto et al. |
| 6,137,291 | A | 10/2000 | Szumowski et al. |
| 6,438,402 | B1 | 8/2002 | Hashoian et al. |
| 6,498,489 | B1 | 12/2002 | Vij |
| 6,624,633 | B1 | 9/2003 | Zou et al. |
| 6,650,926 | B1 | 11/2003 | Chan et al. |
| 7,663,367 | B2 | 2/2010 | Wiggins |
| 2002/0013526 | A1* | 1/2002 | Su et al. .................... 600/422 |
| 2008/0204021 | A1* | 8/2008 | Leussler et al. ............ 324/318 |
| 2012/0249147 | A1* | 10/2012 | Ylihautala ................ 324/318 |

* cited by examiner

*Primary Examiner* — Parikha Mehta
(74) *Attorney, Agent, or Firm* — Stinson Leonard Street LLP

(57) ABSTRACT

An MRI antenna array including a housing and a substrate, antenna elements and circuitry encapsulated by the housing. The housing, antenna elements, and substrate are flexible to allow the housing to distort in three dimensions to closely conform to contours of a patient. The antenna elements are mounted to the substrate in a manner that permits each element to maintain a desired resonance when the housing is distorted in three dimensions. The circuitry is electrically coupled with the antenna elements to maintain tuning and isolation of the elements when the housing is distorted in three dimensions. The housing, antenna elements, and substrate may be elastic to allow the housing to be worn by a plurality of different sized patients so that the housing is in close contact with the patient and conforms to contours of the patient.

15 Claims, 11 Drawing Sheets

GARMENT MRI ANTENNA ARRAY

CROSS-REFERENCE TO RELATED APPLICATIONS

This application is based on and claims priority to U.S. Provisional Application Ser. No. 61/563,413, filed on Nov. 23, 2011, which is incorporated herein by reference in its entirety.

STATEMENT REGARDING FEDERALLY SPONSORED RESEARCH OR DEVELOPMENT

Not Applicable.

BACKGROUND OF THE INVENTION

1. Field of the Invention

The present invention relates generally to magnetic resonance imaging (MRI), and more particularly to flexible and/or elastic MRI antenna arrays for use in receiving MRI signals.

2. Description of Related Art

A. Magnetic Resonance Imaging

Magnetic resonance imaging (MRI) refers generally to a form of clinical imaging based upon the principles of nuclear magnetic resonance (NMR). Any nucleus which possesses a magnetic moment will attempt to align itself with the direction of a magnetic field, the quantum alignment being dependent, among other things, upon the strength of the magnetic field and the magnetic moment. In MRI, a uniform magnetic field $B_0$ is applied to an object to be imaged; hence creating a net alignment of the object's nuclei possessing magnetic moments. If the static field $B_0$ is designated as aligned with the z-axis of a Cartesian coordinate system, the origin of which is approximately centered within the imaged object, the nuclei which possess magnetic moments precess about the z-axis at their Larmor frequencies according to their gyromagnetic ratio and the strength of the magnetic field.

Water, because of its relative abundance in biological tissues and its relatively strong net magnetic moment $M_z$ created when placed within a strong magnetic field, is of principle concern in MR imaging. Subjecting human tissues to a uniform magnetic field will create such a net magnetic moment from the typically random order of nuclear precession about the z-axis. In a MR imaging sequence, a radio frequency (RF) excitation signal, centered at the Larmor frequency, irradiates the tissue with a vector polarization which is orthogonal to the polarization of $B_0$. Continuing our Cartesian coordinate example, the static field is labeled $B_z$ while the perpendicular excitation field $B_1$ is labeled $B_{xy}$. $B_{xy}$ is of sufficient amplitude and duration in time, or of sufficient power to nutate (or tip) the net magnetic moment into the transverse (x-y) plane giving rise to $M_{xy}$. This transverse magnetic moment begins to collapse and re-align with the static magnetic field immediately after termination of the excitation field $B_1$. Energy gained during the excitation cycle is lost by the nuclei as they re-align themselves with $B_0$ during the collapse of the rotating transverse magnetic moment $M_{xy}$.

The energy is propagated as an electromagnetic wave which induces a sinusoidal signal voltage across discontinuities in closed-loop receiving coils, this signal voltage being inversely and non-linearly proportional to the distance between the target voxel and coil element. This represents the NMR signal which is sensed by the RF coil and recorded by the MRI system. A slice image is derived from the reconstruction of these spatially-encoded signals using well known digital image processing techniques.

B. Local Coils and Arrays

The diagnostic quality or resolution of the image is dependent, in part, upon the sensitivity and homogeneity of the receiving coil to the weak NMR signal. RF coils, described as "local coils" may be described as resonant antennas, in part, because of their property of signal sensitivity being inversely related to the distance from the source. For this reason, it is important to place the coils as close to the anatomical region-of-interest (ROI) as possible.

Whereas "whole body" MRI scanners are sufficiently large to receive and image any portion of the entire human body, local coils are smaller and therefore electromagnetically couple to less tissue. Coupling to less tissue gives rise to coupling to less "noise" or unwanted biologically or thermally generated random signals which superimpose upon the desired MR signal. The local coils may be of higher quality factor (Q) than the body coils due to their smaller size. For all of these reasons, local coils typically yield a higher signal-to-noise (S/N) ratio than that obtainable using the larger whole body antenna. The larger antenna is commonly used to produce the highly homogenous or uniform excitation field throughout the ROI, whereas the local coil is placed near the immediate area of interest to receive the NMR signal. The importance of accurate positioning leads to the development of local coils which conform to the anatomy of interest, yet function to permit ease of use.

While the smaller local coil's size works to an advantage in obtaining a higher S/N ratio, this reduced size also presents a disadvantage for imaging deep-seated tissues. Typically, the single-conductor coil diameter which yields the optimal S/N ratio at a depth 'd' is a coil of diameter 'd'; hence, larger diameter single-conductor coils are required to image regions in the abdomen and chest of human patients.

The S/N ratio of the NMR signal may be further increased by orienting two coils, or coil pairs about the imaged object so that each detects RF energy along one of a pair of mutually perpendicular axes. This technique is generally known as quadrature detection and the signals collected are termed quadrature signals.

The outputs of the quadrature coils are combined so as to increase the strength of the received signal according to the simple sum of the output signals from the coils. The strength of the noise component of these signals, however, will increase only according to the square root of the sum of the squares of the uncorrelated noise components. As a result, the net S/N ratio of the combined quadrature signals increases by approximately $\sqrt{2}$ over the S/N ratio of the individual coils.

The quadrature orientation of the two coils introduces a 90° phase difference between the NMR signals detected by these coils. Therefore, combining the outputs from the two quadrature coils to achieve the above described signal-to-noise ratio improvements requires that one signal be shifted to have the same phase as the other signal so that the amplitudes of the signals simply add in phase.

The approximate net gain of $\sqrt{2}$ in S/N ratio is achievable primarily due to the lack of inductive coupling between the coil pairs. This ensures that only the uncorrelated noise components add, in lieu of both the uncorrelated and correlated noise components, to reduce the effective S/N ratio. Inductive isolation is achieved by geometrically orienting the coil conductors such that the mutual inductance is minimized between the coil pairs according to the following:

$$M = \frac{1}{2\pi} \int \frac{I_1(\overline{dl_1}) \cdot I_2(\overline{dl_2})}{|(\overline{r_1}) - (\overline{r_2})|}$$

where M represents the mutual inductance between coils 1 and 2 and the vector components $dl_1$ and $dl_2$ represent segments of coils 1 and 2 with current amplitudes $I_1$ and $I_2$. The denominator represents the magnitude difference of the position vectors of each dl segment. The condition wherein M is approximately zero with respect to the individual self inductances of coils 1 and 2 is known as inductive isolation between the coils.

C. Multiple Channel Receiver/Coil Systems

A method of increasing the S/N ratio of the NMR signal over a larger region is to digitally add the post processed signals derived from more than one coil; each sensitive to the precessing nuclei within overlapping volumes. If two coils' signals are processed and converted into image data separately and then added digitally, one can obtain an increase in S/N ratio (SNR) within the larger volume. Separate amplifiers, analog-to-digital converters, sample-and-hold circuits, computer storage, and image processor channels represent an alternative configuration for processing the two signals in lieu of a single quadrature combiner. A system of four channels whose signals are derived from an array of four coils is described in U.S. Pat. No. 4,825,162. The primary advantage of this system is that one obtains the signal-to-noise performance of smaller surface coils over a larger geometric region corresponding to increased anatomical coverage.

Yet another method of further improving the SNR is to combine the effective gains of both quadrature coils with those of multiple channel or array systems. Such a system of quadrature arrays is comprised of two sets of linear coils, each element in each set having a phase component orthogonal to the phase component of each element of the sister set. Then, the signals are combined such that each linear signal is paired with its co-volume-sharing paired linear coil signal with the appropriate 90 degree phase shift to yield the quadrature gain in each element pair volume. This coil system is taught in U.S. Pat. No. 5,430,378 ('378 patent) entitled "NMR Quadrature Detection Array".

Limitations exists with the aforementioned configuration of quadrature coils; that being that they are not laid out to provide optimal volumetric coverage—that is sensitivity from more than one side of the patient. Due to the fact that they are described as being positioned along one aspect of the patient; the sensitivity profiles imparted are assymetrical to the patient. Two patents referenced have made incremental improvements in volumetric signal homogeneity by creating linear arrays that are positioned above (superior) and below (inferior) the patient. Both U.S. Pat. No. 5,548,218 (Lu) and U.S. Pat. No. 6,624,633 B1 (Zou) employ linear arrays of three or more saddle or butterfly elements posterior to the patient and arrays of three or more single loop elements anterior to the patient. Signals from each anterior and posterior element, arranged opposing each other across the patient volume, are then added in quadrature mixers to create quadrature signals from the medial regions where their signals exhibit the same relative signal strength. These configurations are limited as well due to that simple fact that each element of the quadrature pair has substantially different sensitivity (flux) profiles throughout the medial volume due to their positions being on opposite sides of the volume. Quadrature combination of these signals yields a combined signal that is mostly that signal of the saddle or butterfly coil on those coil's sides of the volume and the combined signal that is dominated by the single loop signal on the single loop side of the volume. It is only in the middle of the volume where the saddle and single loop signals are similar magnitude where effective quadrature gain is realized. So, although the aforementioned patents describe volume coil arrays that provide more homogeneous signal quality throughout a volume, they do not yield the SNR performance locally to the quadrature coil sets described in the '378 patent.

The problem of improved volumetric homogeneity without sacrifice of SNR could be solved by arranging quadrature arrays similar as described in the '378 patent on more than one side of a patient, and of course using care to ensure that element sizes, orientations, and resulting signal phases were such that each element's signals were not destructive to one another. This solution then brings about a two piece coil set that is relatively easy to position about the patient's torso such as presented by U.S. Pat. No. 6,650,926 B1 (Chan et. al.). This particular patent is based upon creating a series of quadrature paired elements overlapping in the Z-direction (long axis of the patient) and held within position of one another by a semi-rigid spline, or spline that is hinged near its center to facilitate some flexibility along the Z-direction. Flexible components of the antenna elements protrude from the central spline and partially wrap about the subject. Opposing anterior and posterior rigid spline coil sets facilitate wrapping from both sides of a patient and creating a uniform quadrature detection volume. This design is limited in the number of elements, has limited flexibility from a generally planar configuration, and doesn't address optimization of multiple elements on such a flexible form.

In the case of the extremities, in contrast to the potentially much larger diameter torso, a different solution is possible that brings the convenience of a singular coil structure versus opposing two-part structures. One solution, presented in U.S. Pat. No. 6,438,402 B1 (Hashoian) is to wrap larger resonating elements about both legs and lower torso with a series of overlapping elements.

Another solution, considering the smaller diameters and lengths of extremities versus the human form, is to place a singular structure of reducing diameter about a single extremity, and with sufficient length and number of elements to optimize the SNR throughout the entire length of the extremity or body part. This concept may appear similar to that of U.S. Pat. No. 6,438,402 B1 (Hashoian), but there exists significant conceptual differences.

First, Hashoian teaches the creation of quadrature pairs of elements within a singular cylindrical wrap, then teaches that multiple wraps can be added in an overlapping fashion; hence creating an array providing considerable longitudinal coverage. For proper tuning to be maintained, the relative flexible antenna structures must maintain their relative shape and position relative to one another; a difficult feat with this mechanical design as there is little that will keep the adjacent structures with the proper critical overlap for the requisite inductive isolation. If the isolation or tuning of an individual element is perturbed due to improper flexing or placement, the uniformity of the exam will be seriously compromised. Secondly, the design requires latching each and every wrapped element separately; a cumbersome task and time sensitive task considering the need for the patient to remain motionless throughout the entire exam and the nature of throughput requirements in MRI.

Thirdly, Hashoian does not teach how to create an array of more than two adjacent quadrature elements; hence compromising the possible SNR compared to an array with all quadrature elements.

Finally, Hashoian does not address optimization of the element size, number, tuning stability or isolation.

Similar antenna geometries of Hashoian are incorporated by Szumowski in U.S. Pat. No. 6,137,291 and Vij in U.S. Pat. No. 6,498,489 B1; however, Szumowski and Vij teach rigid, separable saddle coil pairs or helmholtz pairs versus the flexible elements that Hashoian uses. Both Szumowski and Vij utilize the similar concept of reducing cylindrical diameter to ensure closer coupling to the anatomies in question but neither teaches quadrature elements "surrounding" the anatomies along the entire length of the anatomies.

U.S. Pat. No. 5,435,302 discloses flexible antennas wherein a singular resonator is constructed on a flexible substrate. This patent divulges a method of mounting thin conductors of a single resonator on a preshaped pseudo-flexible form for scanning one unique patient anatomy.

Although U.S. Pat. No. 5,594,339 also teaches some construction methods for creating a flexible coil substrate, it is restrictive in practice as the sheet plastic layers flex in an arch tangential along one axis only. Neither of these two previously mentioned patents teaches coil arrays, or quadrature arrays or the methods required for making such arrays operable (ie. tuning stability, maintaining isolation, and flexing in three dimensions) in a highly flexible environment.

Two more recent patents address the need for multiple elements on shaped forms with contours along all three axes such as a helmet-like coil form or shoulder-torso form. U.S. Pat. No. 6,084,411 ('411 patent) and U.S. Pat. No. 7,663,367 B2 describe the construction of a 3-dimensional form-fitting rigid or fixed position substrate on which independent coil resonators are attached ('411 patent) or manufactured as a traditional overlapping or non-overlapping (for parallel imaging sequence performance optimization) multi-element array as is taught in the scientific literature (many such articles in the Journal of Magnetic Resonance Imaging). Neither patent anticipates a highly flexible antenna array that maintains proper operational capability while being flexed in infinite positions.

BRIEF SUMMARY OF THE INVENTION

The present invention is directed toward an MRI antenna array including a flexible housing, and a flexible substrate, flexible antenna elements and circuitry encapsulated by the housing. The housing is sufficiently flexible to allow it to be draped over or wrapped about a portion of a patient and distort in three dimensions to closely conform to contours of the patient. The antenna elements are attached to the substrate in a manner that permits each element to maintain a desired resonance when the housing is distorted in three dimensions. The circuitry is attached to the substrate and electrically coupled with the antenna elements for maintaining tuning and isolation between the elements when the housing is distorted in three dimensions. The array may be formed as a blanket that may be draped over an patient.

The present invention is also directed toward an MRI antenna array including a flexible and elastic housing, and a flexible and elastic substrate, flexible and elastic antenna elements and circuitry encapsulated by the housing. The housing is sufficiently flexible and elastic to allow it to be worn by a plurality of different sized patients so that the housing is in close contact with the patient and conforms to contours of the patient. The antenna elements are attached to the substrate in a manner that permits each element to maintain a desired resonance when the housing is distorted in three dimensions. The circuitry is attached to the substrate and electrically coupled with the antenna elements for maintaining tuning and isolation between the elements when the housing is distorted in three dimensions. The array may be configured to be worn over any portion of a patient's body, including the pelvis, shoulder, and the entire body.

In another embodiment, the invention is directed toward an MRI antenna array including a flexible housing and a flexible substrate, plurality of antenna elements, and circuitry that are encapsulated by the housing. The housing is lightweight, load bearing, compressible, and insulative and includes a surface for covering a designated portion of a patient. The housing is cut or pressed into a set of connected geometrical shapes positioned between the cut or pressed areas, which allows for smaller bend radii than a non-cut or pressed thick layer. The antenna elements and circuitry are mounted to the substrate, and the circuitry is electrically coupled with the antenna elements.

The present invention is an MRI antenna array constructed in such a way so as to be highly flexible and drape, fit, or conform to a myriad of different shapes and sizes associated with the human anatomy—all while offering optimal S/N ratio from the anatomy in question. Preferably, the invention includes the design of high Q resonating elements from highly flexible conductors whereby they are attached to a flexible, thin, durable substrate which, in combination with element sizing, spacing, and location, keeps them in relative position to one another and maintains isolation amongst the many elements. In addition, one embodiment is to employ elements that are constructed from an electrical conductor which has the properties of expansion/contraction to accommodate stretching with the substrate material to which they are affixed. The attachment points serve also as circuit mounting locations for tuning, matching and isolation components as well as miniature isolation preamplifiers mounted directly in each element's radio frequency current pathway; thus significantly reducing coupling mechanisms and stray loop currents associated with larger circuit boards and component spacing. Preferably, the elements, their isolation and amplification circuitry, and output cabling are embedded in a lightweight, durable, water resistant, biocompatible, cleanable, highly flexible, foam housing. Preferably, the foam housing is thick and compressible enough to be comfortable for the patient to lie upon, yet exhibit a high degree of flexibility along three axes so as to conform to wide ranges of anatomical variations. This accommodation to fitting a range of anatomical sizes ensures that the coil elements are positioned as closely as possible to the target tissues; hence, optimizing the signal derived from the target anatomy based upon minimizing the distance from the target to the antenna elements.

In one embodiment of the invention, stiffeners are added within the encapsulating foam so as to restrict the bending in certain situations whereby the desire is for the flexible array to be self-supporting within a certain region.

In accordance with another embodiment of the invention the elements and associated circuitry are miniaturized and enclosed within the flexible foam housing as described to create garments that may be worn by the subjects in order to specifically target certain anatomies with the best possible anatomical fit of an antenna array so as to yield more optimal S/N ratio from that anatomy. The flexible antenna elements may be attached to a stretchy or elastic material and covered with another layer of the same type of material to create a stretchable garment that fits a range of patient sizes.

The invention also includes a flexible garment with embedded antenna elements that are allowed to contort in shape by a controlled amount and facilitate a certain amount of stretching in the directions of stretch of the garment.

The present invention preferably optimizes coil size, configuration, the number of coil elements or resonators, and the positioning of those resonators about the subject via their being mounted on a flexible substrate, in order to achieve the desired performance, both in terms of S/N ratio, coverage and homogeneity. Further, the resonators are isolated from one another to such a degree so as not to interfere with one another's tuning and performance, and are preferably housed in a water-proof container that facilitates close fitting to the desired patient anatomy via draping the coil over, around or embedding the array within a pull-on garment. Further, these arrays will withstand high degrees of flexing in three dimensions and also withstand the weight of the patient distributed over the surface of the coil housing. Isolation amongst elements is achieved via a combination of two or more mechanisms: 1) geometric isolation between two elements sharing a common sensitivity volume—meaning that their exists little to no inductive coupling between the elements due to their net orthogonal vector sensitivity profiles within the common volume; 2) inductive isolation by means of overlapping elements such that adjacent coil elements have net mutual inductance; 3) reactive isolation by means of a given capacitance or inductance connecting two nearby elements such as to cancel any mutual inductance between the two elements; 4) transformer isolation between two nearby elements whereby currents from each element flow through separate windings of a dual winding transformer in opposite directions and with the proper transformer coupling coefficient to cancel the mutual inductance of the two elements; and 5) the use of low impedance amplifiers and matched input isolation reactances that create a high impedance "trap" to the mutually induced currents from one element to another.

DETAILED DESCRIPTION OF PREFERRED EMBODIMENT

Figure 1:
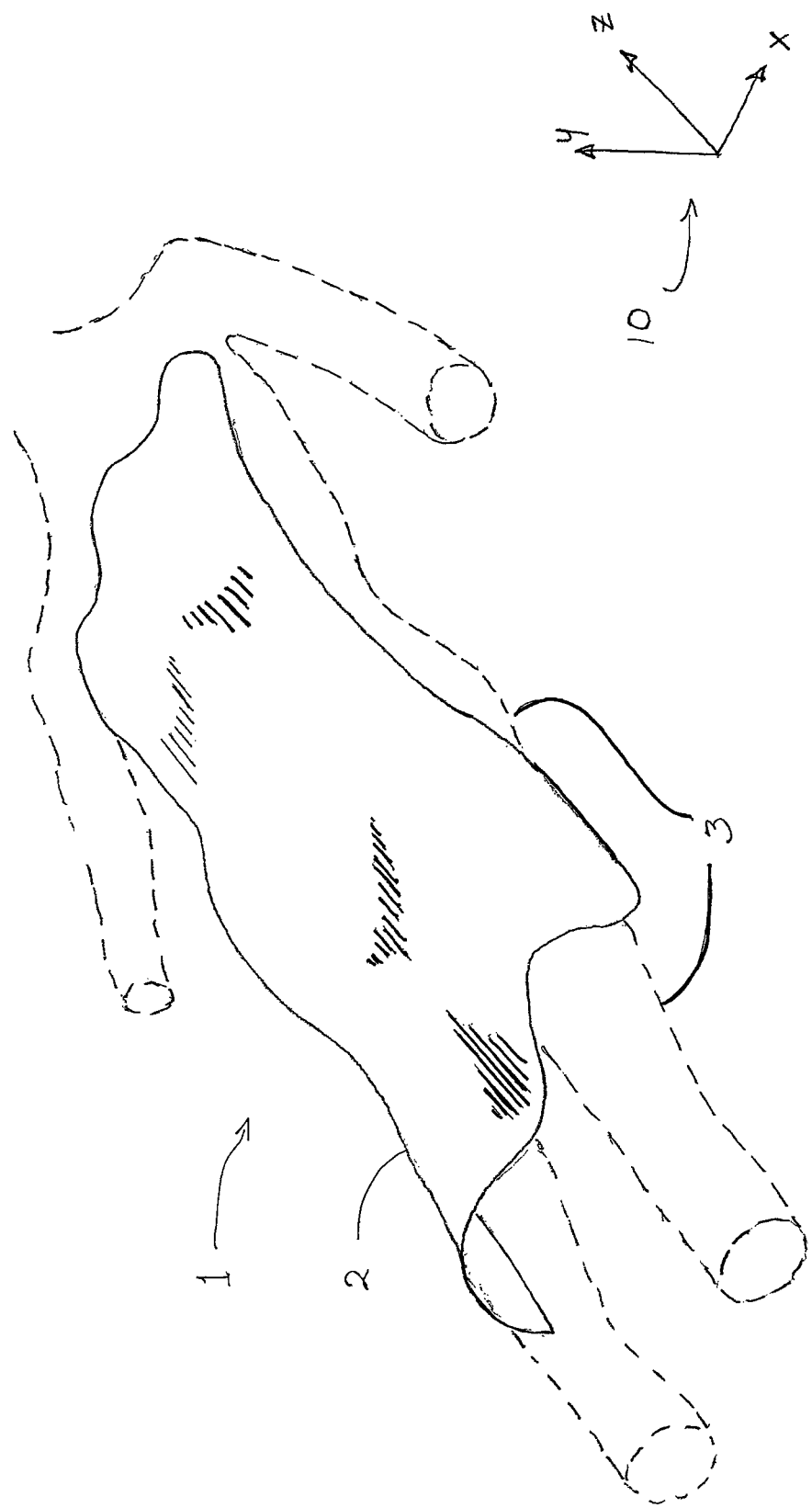
FIG. 1 is a perspective view of a blanket MRI antenna array in accordance with the present invention draped over a person representing one of many complex surfaces that may be covered by the blanket array.

Referring to FIG. 1, a flexible blanket MRI antenna array in accordance with one embodiment of the present invention is shown generally as 1. The blanket array 1 includes sixteen flexible antenna elements (two of which are identified in FIG. 2 as 21) attached to a flexible substrate 2 that is similar to a thin blanket. The elements 21 and substrate 2 are encapsulated by a flexible housing 1B (FIGS. 5A-B), which is preferably constructed from foam and/or fabric as discussed in more detail below, in such a manner that the entire blanket array 1 is sufficiently flexible to drape over or be wrapped about a human body 3 and distort in three dimensions to closely conform to contours of the body 3. This positions the elements 21 closer to the human tissue where they maintain more constant electromagnetic loading and yield more consistent performance results. Consistency is also improved by ensuring a minimum distance between the actual elements 21 and the target anatomy since signal reception decays inversely to distance.

Substrate 2 is preferably constructed of a fire retardant fabric, such as used in some tent fabrics, which exhibits excellent stability and withstands significant sheer stresses. These properties make such a fabric suitable for the substrate 2 to which the elements 21 are attached. An alternate substrate and conductor configuration is very thin Teflon or similar ultrathin sheet plastics to which highly flexible conductors are adhered. The substrate 2, attached elements 21, and foam or fabric housing 1B (FIGS. 5A-B) in combination are sufficiently flexible in order to flex in all three axes and closely contour to protrusions of the human body, such as the legs, breasts or stomach of the human body 3 shown in FIG. 1. This is in contrast to a conventional rigid or hinged rigid coil form that does not facilitate placing the conductors in such close proximity to the desired tissues due to bending and flexing restrictions. A three dimensional coordinate system 10 is shown in certain of the drawings relative to the patient and MRI antenna array. The Z axis of the coordinate system 10 is aligned with the long axis of a patient (from head to toe), the Y axis is aligned with the anterior/posterior direction, and the X axis is aligned with the left/right direction.

Figure 2:
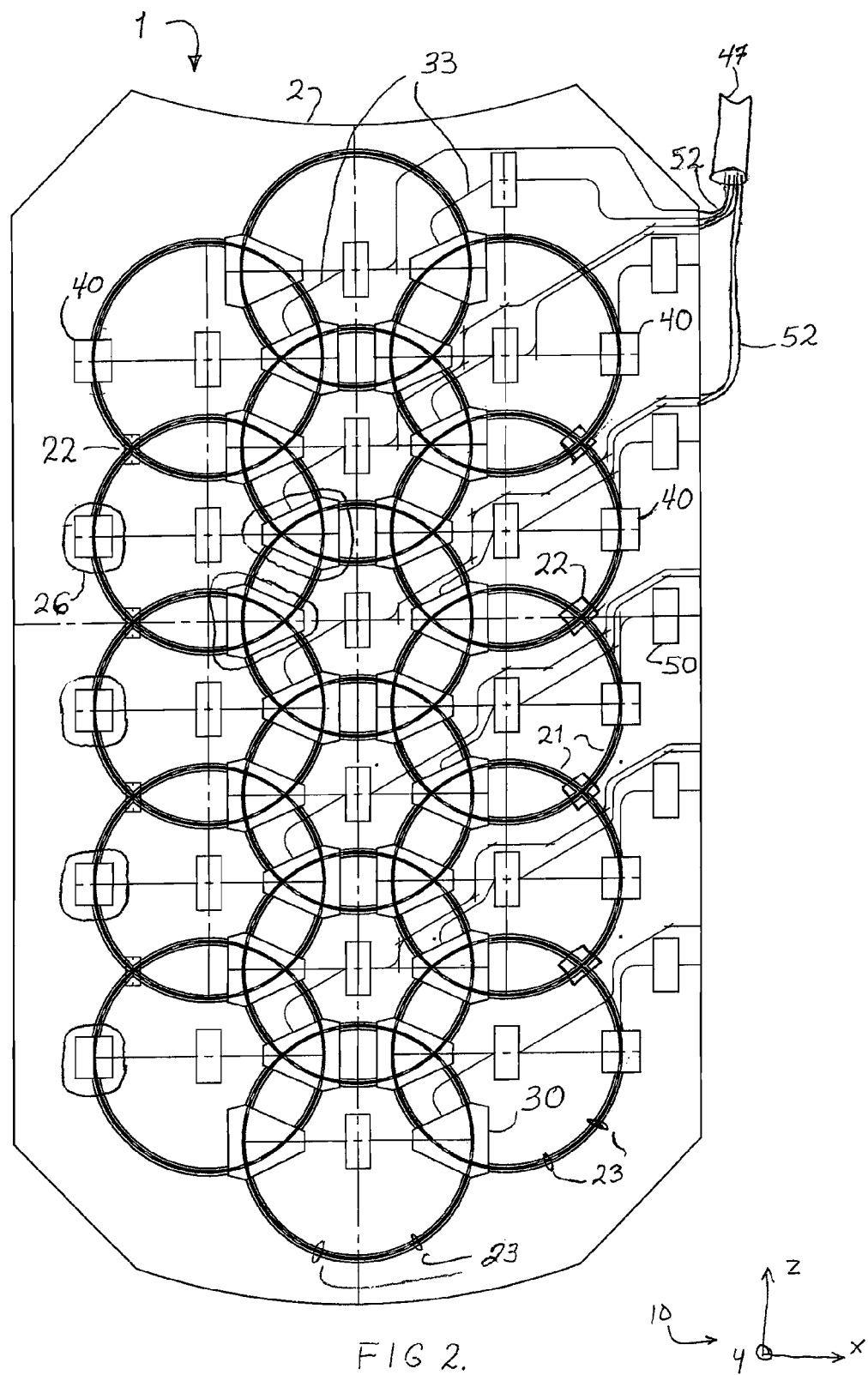
FIG. 2 is a plan view showing the layout of antenna elements and circuit boards of the blanket array of FIG. 1.

Referring to FIG. 2, blanket array 1 includes sixteen elements, two of which are identified in the drawings as 21, each of which mounted to flexible substrate 2 in a manner described below that permits the array 1 to drape over a patient and closely follow a myriad of contour variations, such as shown in FIG. 1. Blanket array 1 is suitable to be used for imaging the more broad ranging target anatomies of whole body or spine MRI; yet, smaller versions of the embodiment could be used to wrap around extremities or pediatric torsos. Elements 21 are preferably sized to allow adequate penetration to deep seated tissues. Elements 21 are configured to overlap and may be non-overlapping and positioned in order to optimize parallel image processing speed (acceleration factors) and/or image quality. Blanket array 1 includes sixteen elements 21 in order to correspond with the increasingly popular MRI platform containing sixteen simultaneously active channels wherein each channel has its own analog-to-digital (A/D) converter and data processing. Blanket array 1 results in better image quality from the deeper seated tissues, and accommodates acceleration sequences.

Each of the sixteen elements 21 includes a loop of high Q extremely flexible conductor, preferably a coaxial cable with the outer insulator removed and split at a minimum of two junction points by rigid circuit boards 30 or 40 and 22. There are three overlapping columns of elements 21. The leftmost and rightmost columns each include five elements 21, and the centermost column includes six elements 21. Adjacent elements 21 within each column overlap, and the elements 21 of adjacent columns overlap. Circuit boards 30 are positioned at the locations where the centermost column of elements 21 overlaps elements 21 in the right and left columns, and also at the locations where adjacent elements 21 within the centermost column overlap and at one of the two locations where adjacent elements 21 within the left and right columns overlap nearest the center column. Circuit boards 40 are positioned at the other of the two locations where the elements 21 within the right and left columns overlap away from the center column. There are twenty-two circuit boards 30, although only a few are numbered in the drawing for clarity. On the top two circuit boards 30 and bottom two circuit boards 30, an element 21 from the centermost column overlaps a single element 21 from either the left or right column. For half of the remaining eighteen circuit boards 30, adjacent elements 21 from the centermost column overlap, and one of the elements 21 from the left or right columns overlaps each of the adjacent elements 21 from the center column. For the other half of the remaining eighteen circuit boards 30, adjacent elements 21 from one of the left or right columns overlap, and one of the elements 21 from the center column overlaps each of the adjacent elements 21 from the right or left column. There are eight circuit boards 22, although only a few are numbered in the drawing for clarity. Circuit boards 22 are positioned at locations where adjacent elements 21 in the right and left columns overlap. There are ten circuit boards 40, although only a few are numbered in the drawing for clarity. Each circuit boards 40 is positioned at a location on one of the elements 21 from the right or left columns that is positioned farthest from the center column of elements 21.

As described in more detail below, circuit boards 22, 30 and 40 contain the distributed capacitance required for resonance of the elements 21. Boards 30 and 40 also serve the purposes of decoupling and impedance matching. Not all of the larger boards 30 and 40 have identical electrical circuitry because each element 21 only needs one board 30 or 40 with all of the aforementioned circuitry. The larger hexagonal boards 30 also serve the purpose of stability attachment plates for the flexible elements 21 crossing them (see FIG. 3) in order to, in part, maintain the desired overlap or gap between adjacent elements 21. All circuit boards 22, 30, and 40 are preferably small in dimension or footprint so as to have less negative effect on the overall flexibility of the blanket array 1. Elements 21 are made from coaxial cable due to its high conductivity properties or Q (clad copper) resulting from high shield effectiveness (>99%) of the original coaxial cable. The shield of the coaxial cable is used as the radio frequency current carrier or coil inductive conductor, and the center conductor of the coaxial cable is used, when desirable, for carrying decoupling DC currents to other circuit boards 22, 30, and/or 40.

Figure 3:
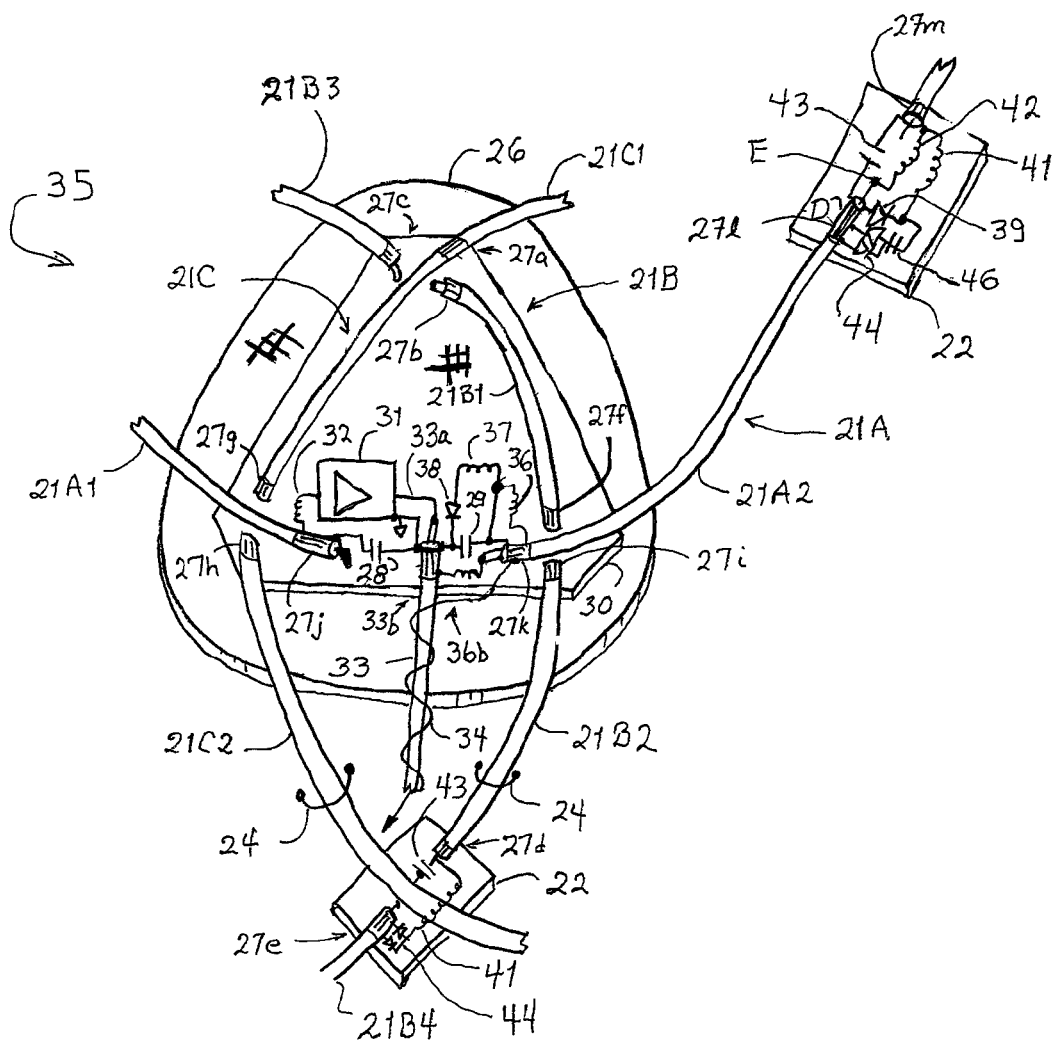
FIG. 3 is a detail view of three circuit boards and a portion of three antenna elements of the blanket array of FIG. 1.
Figure 9:
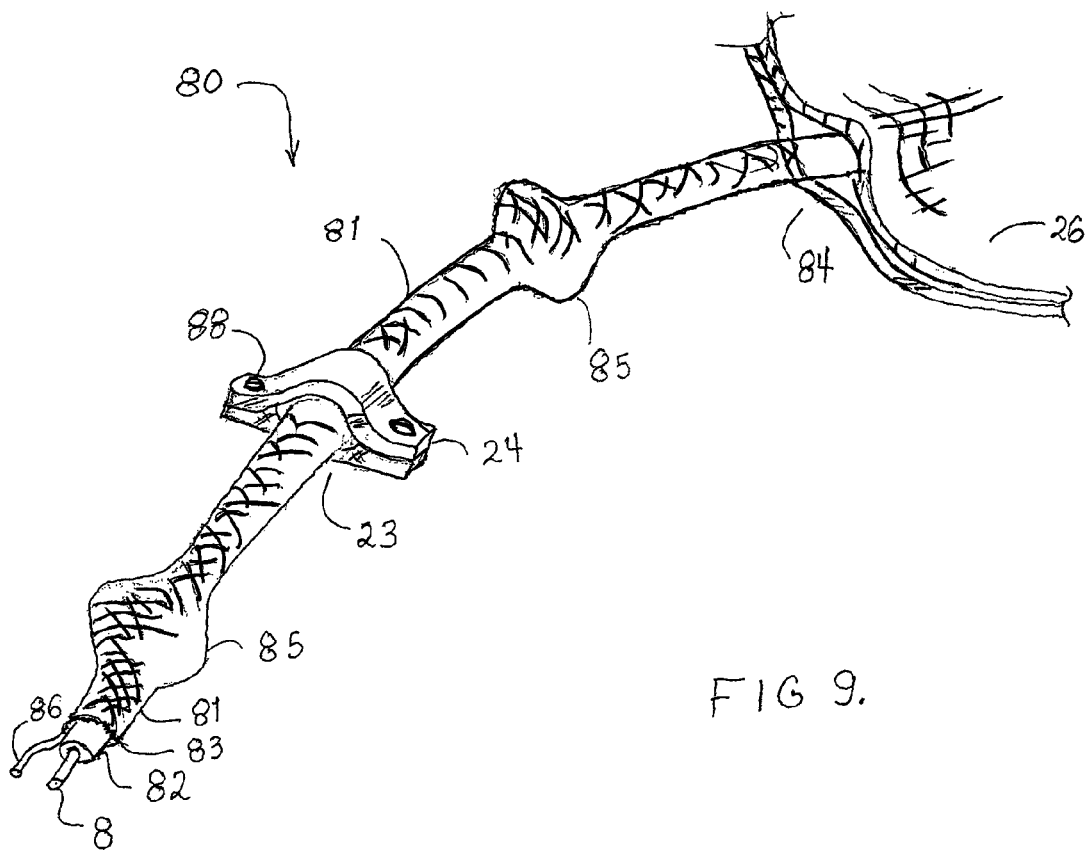
FIG. 9 is a perspective view of an elastic or stretchable conductor of the pelvic array shown in FIG. 7.

All circuit boards 22, 30, and 40 and the flexible elements 21 are fastened to the flexible substrate 2 at select points so as to have minimal negative influence on the general three dimensional flexibility of the blanket array 1. For example, each of the circuit boards 22, 30, and 40 is preferably mounted to substrate 2 near its center using plastic rivets or nylon screws. Other mounting methods are within the scope of the present invention. Each element 21 is joined to substrate 2 with a plurality of loosely fitting tie clamps or eyelets 24 of plastic or thread at points 23 which are generally equidistant from each other and boards 22, 30, and 40 along the longest span of the element 21 between two boards 22, 30, and 40. Tie clamps 24 are positioned such that a section of element 21 will slip/move through the clamps 24 and distort nominally with flexing, yet distort a restricted amount such that the element 21 maintains its general shape, and therefore resonance when the array 1 is draped over or wrapped about a patient and distorted in three dimensions. The clamps 24 may be simple arch shaped loops as shown in FIG. 3, or have a slightly more complex two piece design as shown in FIG. 9.

Further, the shield portion of the coaxial cable elements 21 are mounted to boards 22, 30, and 40, preferably by soldering, in certain locations as more fully described below in order to maintain the relative positioning of the adjacent elements 21 and general shape of each element 21. Referring to FIG. 3, which shows an assembly 35 including one of the boards 30 on which three of the elements 21 overlap, those elements referred to as 21A, 21B, and 21C, portions of the elements 21A, 21B, and 21C are joined to board 30. Element 21A includes element portions 21A1 and 21A2, element 21B includes element portions 21B1, 21B2, 21B3, and 21B4, and element 21C includes element portions 21C1 and 21C2. Element portion 21C1 is mounted to board 30 at locations 27*a* and 27*g*, element portion 21B1 is mounted to board 30 at locations 27*b* and 27*f*, element portion 21B3 is mounted to board 30 at location 27*c*, element portion 21A1 is mounted to board 30 at location 27*j*, element portion 21A2 is mounted to board 30 at location 27*k* and to board 22 at location 27*l*, element portion 21B2 is mounted to board 30 at location 27*i* and to board 22 at location 27*d*, element portion 21C2 is mounted to board 30 at location 27*h*, and element portion 21B4 is mounted to board 22 at location 27*e*. Another portion of element 21A is mounted to board 22 at location 27*m*. At each of the tie points 27*a-m* where FIG. 3 shows a gap in one of the elements 21, the shield portion of the coaxial cable element 21 is mounted to the board 30. Board 30 is constructed to provide a continuous connection of the above-mentioned locations 27*a-m* such that each of elements 21A-C is continuous as it passes through the board by way of vias at locations 27*a-m* which connect to traces (not shown) on the back side of the board thus providing a circuit path underneath the overlapping element 21. For example, element portion 21B3 enters the board 30 and is soldered at 27*c*, which is connected to a via which passes through the board 30 to a conductor on the back side of the board 30 and runs generally straight to underneath point 27*b* of element portion 21B1 where it connects to another via which passes through the board 30 and is connected to point 27*b*, thus completing the circuit continuity of element portions 21B3 and 21B1. Similarly connected point pairs on board 30 are 27*g* to 27*h* and 27*f* to 27*i*, and on boards 22 are 27*l* to 27*m* and 27*d* to 27*e*. The remainder of the elements 21 shown in FIG. 2 are mounted to respective boards 22, 30, and 40 over which they pass in a similar manner as described above with respect to elements 21A, 21B, and 21C. The locations, or tie points, 27*a-m* are strategically placed in order to maintain a relatively constant gap between those adjacent elements 21A, 21B, and 21C (FIG. 2) and more specifically, with respect to the portion of the elements that pass over board 30, maintain the area circumscribed by element portions 21A1, 21A2, 21B1, 21B2, 21C1 and 21C2. This maintains tuning and isolation between adjacent and nearby elements 21 when the array 1 is draped over or wrapped about a patient and distorted in three dimensions. Routing the shield conductor portions of the elements 21 underneath the board 30 in this manner allows the shield conductor portions to be continuous, but also keep a low profile so that it is not uncomfortable for a patient to lie upon the board 30. There are additional tie points 23, shown in FIG. 2, which restrict the shape distortion but facilitate flexing of elements 21.

The difference between boards 30 and 40 is the shape of the boards 30 and 40, and that the boards 30 include the physical tie down points 27*a-c* and 27*f-k* for three overlapping elements 21, while boards 40 only include physical tie down points for one element 21. Each of boards 30 is hexagonal with a first set of three sides of approximately equal length and a second set of three sides of approximately equal length that are shorter than the first set of sides. The shorter sides alternate with the longer sides to form the board 30. The shape of boards 30 allows the boards 30 to maintain a desired spacing between the elements 21A-C. Each of boards 40 is rectangular. As shown in FIGS. 2 and 3, boards 30 and 40 are encapsulated by protective layers 26, which are preferably constructed from foam and/or flexible rubberized plastic similar to an automobile tire inner-tube patch. There is one layer 26 positioned on each side of the boards 30 and 40 to serve as insulative covering as well as strain relief for elements 21 and preamplifier cables 33 exiting the boards 30 and 40. In FIG. 3, only one of the layers 26 is shown so that the rest of board 30 is visible. In FIG. 2, only certain of the boards 30 and 40 are shown with layers 26 for clarity. The layers 26 provide strain relief by adhering strongly to the elements 21 and preamplifier cables 33 from both sides and providing a restriction on the bending moment of the elements 21 and preamplifier cables 33 as they exit the boards 30 and/or 40.

Eleven of the boards 30 and five of the boards 40 contain the same electrical circuitry, which is shown on the board 30 in FIG. 3 and described in detail below. Referring to FIG. 2, the boards 30 containing this electrical circuitry are the five boards 30 positioned between the left and center columns of elements 21 and having a short side pointing to the left of the array 1, and the six boards positioned between the center and right columns of elements and having a short side pointing to the left of the array 1. The five boards 40 containing this circuitry are the boards on the right hand side of the array 1. Each of these eleven boards 30 and five boards 40 includes the matching, tuning, active decoupling, and amplifier circuitry shown in FIG. 3 for one of the sixteen elements 21. Board 40 is smaller in footprint than board 30 in order to optimize the overall flexibility of the blanket array 1 while housing the same requisite circuitry as board 30 less the added footprint for stabilizing the intersection of three elements 21A, 21B, and 21C such as shown in FIG. 3. The remainder of the boards 30 and 40 shown in the drawings do not include this circuitry, but do include tie down points similar to the points 27*a*-1 shown in FIG. 3 for maintaining the desired shape and relative position of the elements 21.

Referring to FIG. 3, the circuitry on the eleven of boards 30 and five of boards 40 identified above is described below. The circuitry is compact, which reduces or eliminates unwanted stray reactances of stray loop currents and long lead lengths among the components. The compactness also aids the flexibility and durability of the blanket array 1. A matching capacitor 28 and decoupling capacitor 29 are connected in series with the shields of element portions 21A1 and 21A2 across the gap between those portions as follows. One side of capacitor 28 is connected to (the shield of) element portion 21A1 and the other side is connected to one side of capacitor 29, to the shield 33*b* of preamplifier cable 33, to the preamplifier 31 ground, and to a decoupling diode 38. The other side of capacitor 29 is connected to (the shield of) element portion 21A2. An isolation inductor 32 is connected on one side to the shield of element portion 21A1 and on the other side to a preamplifier 31 input. The other signal connection to the input of the preamplifier 31 is the common connection 33*b* described above. Signal developed across capacitor 28 is delivered to preamplifier 31 via isolation inductor 32, and the amplified signal output from preamplifier 31 is connected to the cable 33 center pin 33*a*. Signal output is then connected across the center pin 33*a* to shield common 33*b*. In this preferred embodiment, the preamplifier 31 operating voltage is also brought to the amplifier via the preamplifier cable 33 (center pin 33*a* with respect to shield 33*b*) and system cable 52 through Balun 50, which reduces wiring and circuitry.

Each of the eleven boards 30 and five boards 40 identified above with the circuitry shown in FIG. 3 have a preamplifier cable 33, which connects the board 30 or 40 to the MRI system (not shown) via a Balun 50 and system cable 52 (FIG. 4), as described below. Other mother boards or routing boards (not shown) may be positioned between the Balun 50 and MRI system (not shown). As shown in FIG. 2, the preamplifier cables 33 from the boards 30 and 40 enter a Balun 50, and a system cable 52 exits the Balun 50 and merges into a bundle 47 which is terminated at a system connector (not shown) of the blanket array 1. For clarity, FIG. 2 only shows six of the system cables 52 exiting the substrate 2. There are ten other system cables 52 that exit the substrate 2 at the locations shown on FIG. 2 where there are horizontal lines perpendicular to the right edge of substrate 2.

Decoupling current is brought to the board 30 circuitry shown in FIG. 3 via an independent twisted wire 34, which is twisted to avoid any EMF induced on the wire with respect to the shield of coaxial preamplifier cable 33. The side of decoupling capacitor 29 that is connected to the shield of element portion 21A2 is also connected to one end of a decoupling inductor 37. The other end of the decoupling inductor 37 is connected to one end of a diode 38. The other end of the diode 38 is connected between the capacitors 28 and 29. Wire 34 is joined to one end of an RF isolation choke (inductor) 36 and the other end of inductor 36 is connected between decoupling capacitor 29 and a decoupling inductor 37. Decoupling voltage and current is applied via wire 34 and inductors 36 and 37 to the diode 38 with return path for this current on the coaxial shield 33*b*. When the decoupling voltage provides sufficient forward bias to the diode 38, it conducts, effectively placing inductor 37 in parallel with capacitor 29, which creates a high impedance to the designated RF resonance of the element 21A and decouples it from the transmit pulse.

There are two boards 22 shown in FIG. 3, the one in the upper right hand portion of FIG. 3 includes active and passive decoupling circuits, and the one positioned underneath board 30 includes only a passive decoupling circuit. The active and passive decoupling circuits on board 22 are optional. Boards 22 serve two purposes, the first as a minimal mechanical footprint for flexibility reasons that also provides for a low profile circuit crossover of two elements 21 as described with connections 27*a-c* on board 30. Secondly, the board 22 footprint may be populated with the added decoupling circuitry described below when such circuitry is warranted to increase the power handling capacity of the total decoupling circuitry—more decoupling junctions being required for larger element areas as is well known in the industry. The optional active and passive decoupling circuitry on board 22 are discussed below. A secondary active decoupling circuit can optionally be biased using the same wire 34 connected to the conductor shield 27k through an isolation inductor similar to 36, in which case inductor 36 would not connect to 37 as shown but instead to 27k of element segment 21A2. The other end of element portion 21A2, connection 27l, connects to diode 39, which connects then to decoupling inductor 41 which then serially connects to connection 27m, then to RF choke/inductor 42, then to the return bias path via the same conductor segment 21A2 center conductor E. Center conductor E connects to one end of another isolation choke (inductor) 36b the other end of which is connected to the common return or the shield 33b of preamplifier cable 33 thus creating two parallel and equally resistive (DC) circuit pathways to two independent decoupling diodes, one 38 on board 30 and the other 39 on board 22.

The optional DC bias enters independent decoupling board 22 via the shield D and activates decoupling diode 39, which when on creates a high impedance trap to the tuned operating frequency, the trap consisting of decoupling inductor 41, and resonant capacitor 43. One end of decoupling diode 39 is joined to shield 27l and the other end is joined to an end of decoupling inductor 41. The other end of decoupling inductor 41 is joined to an end of return isolation inductor 42. The other end of return isolation inductor 42 is connected to center conductor E. Resonant capacitor 43 is connected to shield 27l and the shield 27m of the other portion of element 21A exiting board 22. Inductor 41 is tuned to resonate with capacitor 43 and create the requisite high impedance to the element frequency during the system transmit pulse—synchronized with the DC bias. A second specially designed Schottky back-to-back (reverse polarity) diode pair 44 with DC blocking capacitor 46 is in parallel with the active diode 39. This diode pair 44 fires on during the transmit pulse when sufficient energy is developed across the capacitor 43 and inductor 41 in the event that there is no active diode 39 or that it doesn't activate properly. The diode pair 44 is a safety redundancy when there is an active diode 39, or it is an alternate decoupling strategy when there is no active diode 39. This embodiment represents one rendition of decoupling and may vary depending on the MRI system outputs. The board 22 positioned under board 30 and which includes only passive decoupling circuitry, includes the inductor 41, capacitor 43, and diode pair 44 connected in the same manner as discussed above with respect to the other board 22.

Capacitors 28, 29 and 43, all effectively in series, are chosen such that their combination results in resonance with the total loop inductance 21A. The independent values of those capacitors are as follows. Capacitor 28 is chosen to yield approximately 50 ohms to the input of the low impedance input amplifier 31. The reactance of capacitor 28 is matched by an equal and opposite reactance of inductor 32 such that the pair creates a high impedance to RF current flows on the loop 21, which provides the desired isolation benefit of the low impedance amplifier 31. Capacitor 29 creates a ratio of impedances, along with capacitor 43, with the matching capacitor 28. Therefore, these capacitors 28, 29, and 43 are all selected by employing reactance formula and iterating by trial and error to obtain the optimal effect of match, isolation given the input characteristics of a given preamplifier 31 and decoupling efficiency.

The preamplifier cable 33, which connects the preamplifier 31 output to the control board or MRI scanner (not shown), requires isolating the common ground of the system from that of the preamplifier 31 and circuitry of assembly 35. This is best achieved with a tuned trap or Balun 50 (FIG. 4) created out of the shield of coaxial cable as described below. There are sixteen Baluns 50, one for each element 21, each joined with a preamplifier cable 33 leaving one of the eleven boards 30 or five boards 40 identified above and the system cable 52 identified with the board 30 or 40. Only two of the Baluns 50 are numbered in FIG. 2 for clarity. The Baluns 50 shown in FIG. 2 include the top five elongated rectangles positioned in the center of the center column of elements 21, the five elongated rectangles positioned in the center of the right column of elements 21 along with the single elongated rectangle positioned above the right column of elements 21, and the five elongated rectangles positioned to the right of the right column of elements 21. There are six additional elongated rectangles shown in FIG. 2, but not numbered, which include no circuitry but are optionally included in the blanket array 1 to maintain symmetry for aesthetics. In the preferred embodiment then, all preamplifier cables 33 run through a separate "floating" Balun 50, and a system cable 52 exits the Balun and is then merged into a thin bundle of coaxial cables 47. This cable bundle 47 is strategically positioned near the exit point of the blanket array 1 so as not to impede the flexibility of the blanket array 1.

Figure 4:
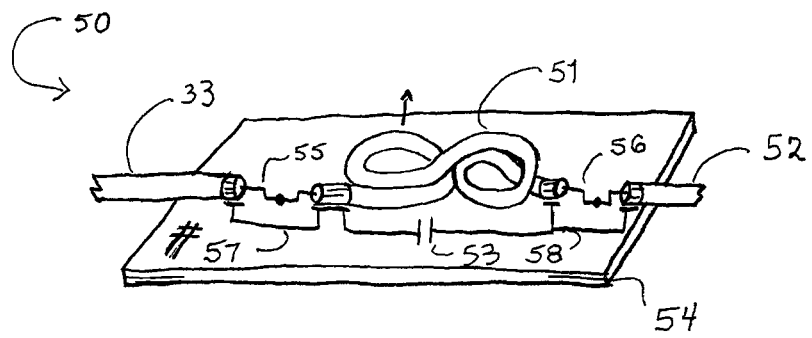
FIG. 4 is a detail view of a low profile, magnetic field neutral, cable Balun of the blanket array of FIG. 1.

Referring to FIG. 4, each Balun 50 includes a board 54 to which the shield portions of coaxial cables 33 and 52 are mounted. A stacked figure eight set of windings made from a miniature rigid coaxial cable 51 is mounted to the board 54 between the preamplifier cable 33 and system cable 52. The center conductors of the cables 33, 51, and 52 are connected via wires 55 and 56, and the shields of cables 33, 51, and 52 are connected via wires 57 and 58. A capacitor 53 is connected between the shield ends of cables 33 and 52. The Balun 50 is created by the inductance of the figure eight winding of cable 51, and therefore it is dependent upon the number, size, length and spacing of the windings of cable 51. FIG. 4 depicts only two windings for simplicity; however, several may be required to yield the desired isolation effect. The total inductance of cable 51 is resonated with capacitor 53. By keeping the cable 51 small and limiting the number of its windings, the height of the assembly can be kept less than 5 mm so as to present a minimal obstacle to cover and pad against eventual patient pressure. Also, by keeping the board 54 small and tethered only by the cables 33 and 52, the flexibility of the completed blanket array 1 is maintained.

Figure 5A:
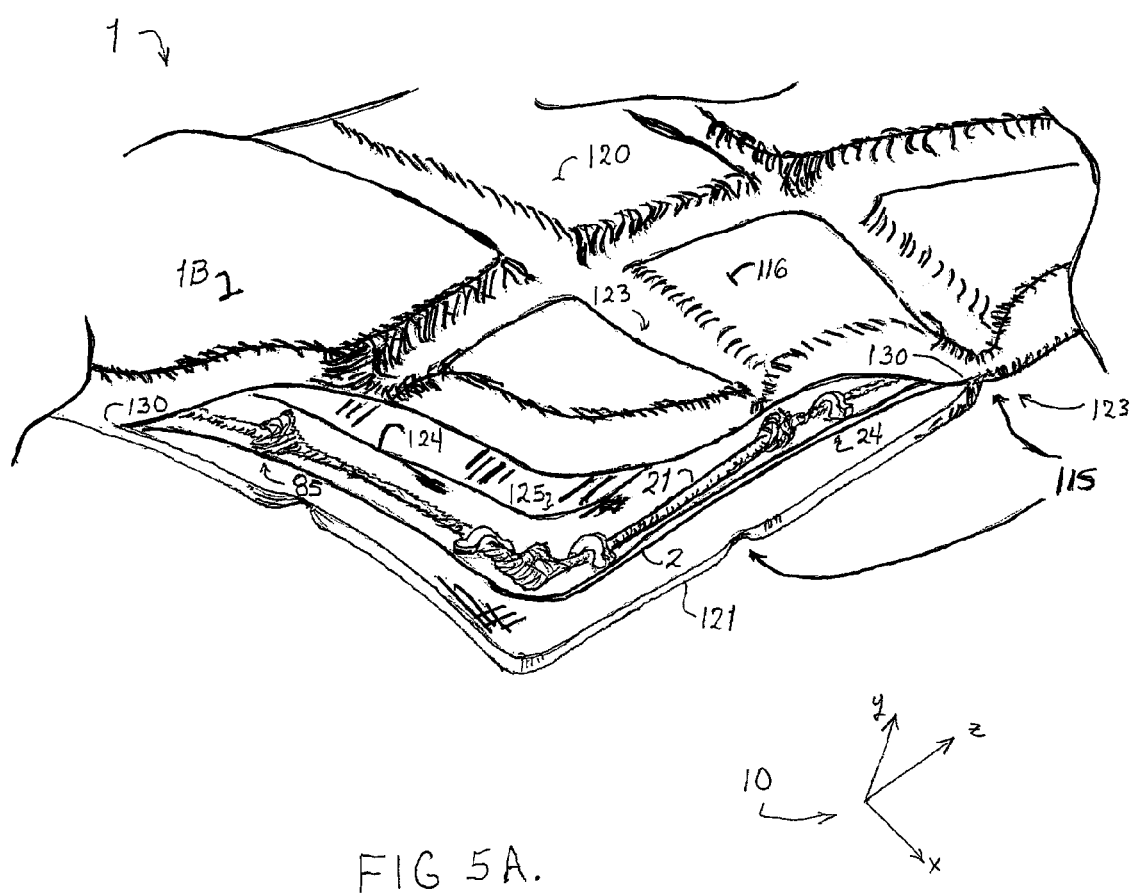
FIG. 5A is a perspective view of one corner of the blanket array of FIG. 1 showing a foam housing which is partially separated showing a substrate encapsulated by the housing.

Referring now to FIG. 5A, blanket array 1 includes a flexible housing 1B, preferably constructed from compressed EVA foam, that encapsulates the substrate 2, elements 21, boards 22, 30 and 40, Baluns 50, and cables 33 and 52. FIG. 5A shows a portion of the foam housing 1B cut open at points 130 and peeled apart so that a portion of substrate 2 may be seen. The foam housing 1B includes a top layer 120 joined to a bottom layer 121. The top layer 120 and bottom layer 121 include aligned grooves 115 and non-grooved regions 116 that are thicker than the grooves 115. The grooves 115 are preferably cut or pressed into the layers 120 and 121, to form the geometrical shapes of the non-grooved regions 116. The grooves 115 allow for a smaller bend radii of the array 1 then if the housing 1B was formed from layers 120 and 121 that did not include any grooves 115. The non-grooved regions 116 of the top layer 120 have a thickness of between approximately 0.50 to 0.75 inches, and most preferably approximately 0.625 inches. The non-grooved regions 116 of the bottom layer 121 have a thickness of between approximately 0.25 to 0.40 inches, and most preferably approximately 0.25 inches. The thickness of the non-grooved regions 116 of the top layer 120 and bottom layer 121 in combination is between approximately 0.75 to 1.15 inches, and most preferably approximately 0.875 inches. The thickness of the blanket array 1 at the grooves 115 is between approximately 0.14 to 0.20 inches, and is most preferably approximately 3/16 of an inch. The non-grooved regions 116 of the top layer 120 have a thickness that is sufficient to cover, pad, and seal the circuit boards 22, 30, 40, Baluns 50, cables 33 and 52 and clamps 24. The non-grooved regions 116 may also be hollowed out, or thinner in certain areas, as necessary to maintain a uniform compression of the foam over the various thicknesses of the components covered by the foam. The thickness of the grooves 115 permits the blanket array 1 to flex at the grooves 115 so that it is able to closely conform to and cover body parts having different contours.

Top and bottom layers 120 and 121 of foam extend beyond the perimeter of the substrate 2 to which the elements 21 and their clamps 24. This provides the layers 120 and 121 with a sufficient area to bond together under compression so that they seal liquid and contaminants from entering between the layers 120 and 121. Further, substrate 2 is discontinuous in certain areas, one of which is identified in FIG. 5A as 124, in order to provide additional areas 125 where the layers 120 and 121 may bond together. The housing 1B is preferably light weight, flexible, load bearing, compressible, and insulative.

FIG. 5A also illustrates that conductor 21 has bulges, one of which is identified as 85 and is discussed below in connection with FIG. 9, which expand and contract to allow the conductor 21 to stretch thereby creating additional flexibility and elasticity in the conductor 21 and blanket array 1. The foam layer 120 includes pockets to accommodate the bulges 85 and their expansion and contraction.

Figure 5B:
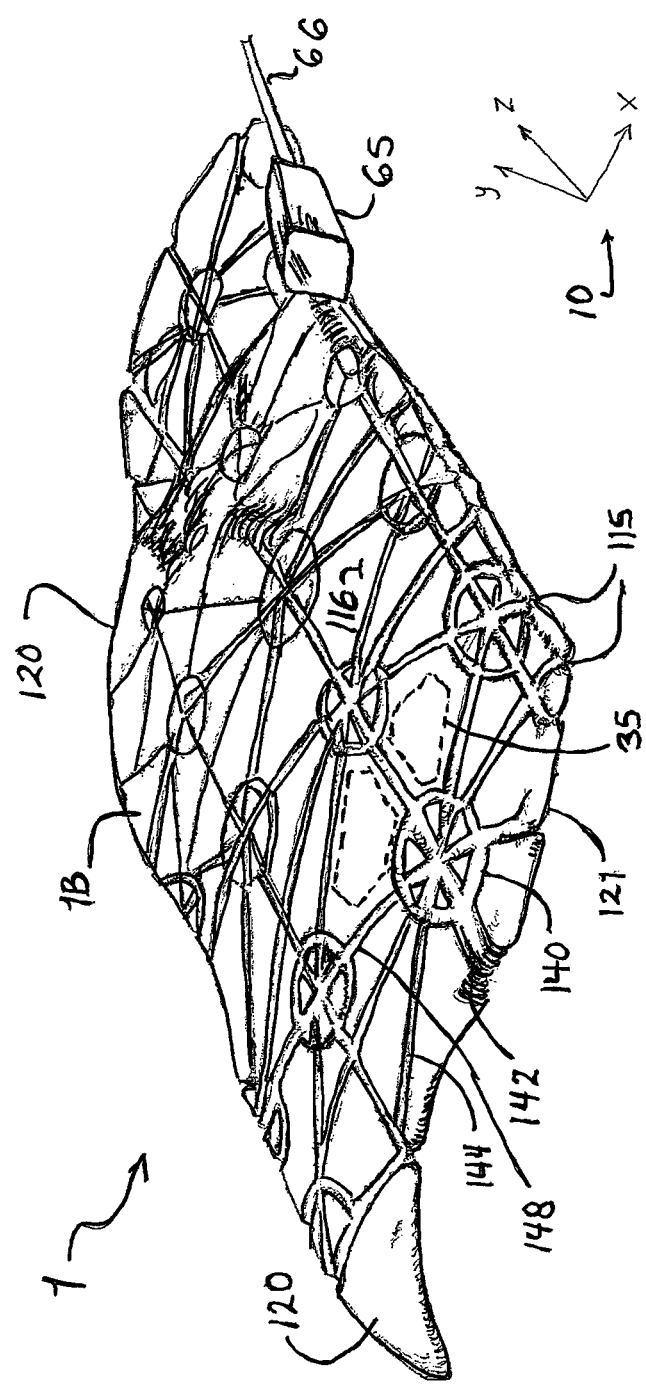
FIG. 5B is a perspective view of a portion of the blanket array of FIG. 1 showing a pattern of grooves in the foam housing.

FIG. 5B shows the overall textured pattern of grooves 115 and non-grooved regions 116 of the blanket array 1, which yields flexibility along all groove 115 directions. The grooves 115 form a repeating pattern of circles, one of which is shown as 140, and lines 142, 144, and 148 intersecting in the center of each circle 140. There is an angle of approximately 60 degrees between lines 142 and 144, between lines 144 and 148, and between lines 148 and 142. The circles 140 are centered within the circular elements 21, shown in FIG. 2. Two of the hexagonal assemblies 35 are shown in dashed lines in their position within the blanket array 1. The assemblies 35 are shaped in order to promote flexibility of the blanket array 1. Grooves 115 are positioned around the perimeter of the assemblies 35 so that the blanket array 1 may flex in all directions around the assemblies 35. The boards 22, 30 and 40 and Baluns 50 are preferably positioned in the non-grooved regions 116. The antenna elements 21 and cables 33 and 52 cross over the grooves 115. Inside of the grooves 115, the elements 21 and cables 33 and 52 are preferably positioned within tubes (not shown) having a relatively small diameter that is just larger than the diameter of the elements 21 and cables 33 and 52. The tubes (not shown) allow the elements 21 and cables 33 and 52 to move through the tubes as the blanket array 1 flexes in order to prevent the elements 21 and cables 33 and 52 from breaking and to promote flexibility of the array 1. The outer surfaces of all of the non-grooved regions 116 preferably lie in the same parallel or generally curvilinear plane in order to present a relatively even pressure distribution on a patient using the blanket array 1. The bundle 47 of cables 52 is routed to a system cable junction board (not shown) housed within a plastic housing 65 that is mounted to the perimeter of the foam housing 1B. The board within housing 65 connects the bundle 47 of cables 52 to a cable 66 that connects the blanket array 1 to a MRI system receptacle (not shown). The housing 65 may include a quick disconnect receptacle connector (not shown) for the electrical connections within the cable bundle 47. The housing 65 may also include a strain relief (not shown) for the cable 66 where it enters the housing 65.

Instead of being constructed from foam with grooves, housing 1B may simply be constructed from flat sheets of an elastic material such as neoprene that encapsulate the elements 21, circuit boards 22, 30 and 40 and Baluns 50, and cables 33 and 52. Further, in this construction, a layer of foam may be positioned between the elastic sheets with cut out or compressed regions that are aligned with, and a thickness that corresponds with, the elements 21, circuit boards 22, 30, and 40 and Baluns 50, and cables 33 and 52 such that the overall thickness of the array is approximately the same in any given location. Other layers, such as layers that are waterproof or layers for comfort, may also form a part of the housing 1B.

In one embodiment, the components described above making up array 1 are formed from relatively small, lightweight materials so that the array 1 may be draped over an infant patient so as not to compromise the patient's breathing.

Figure 6:
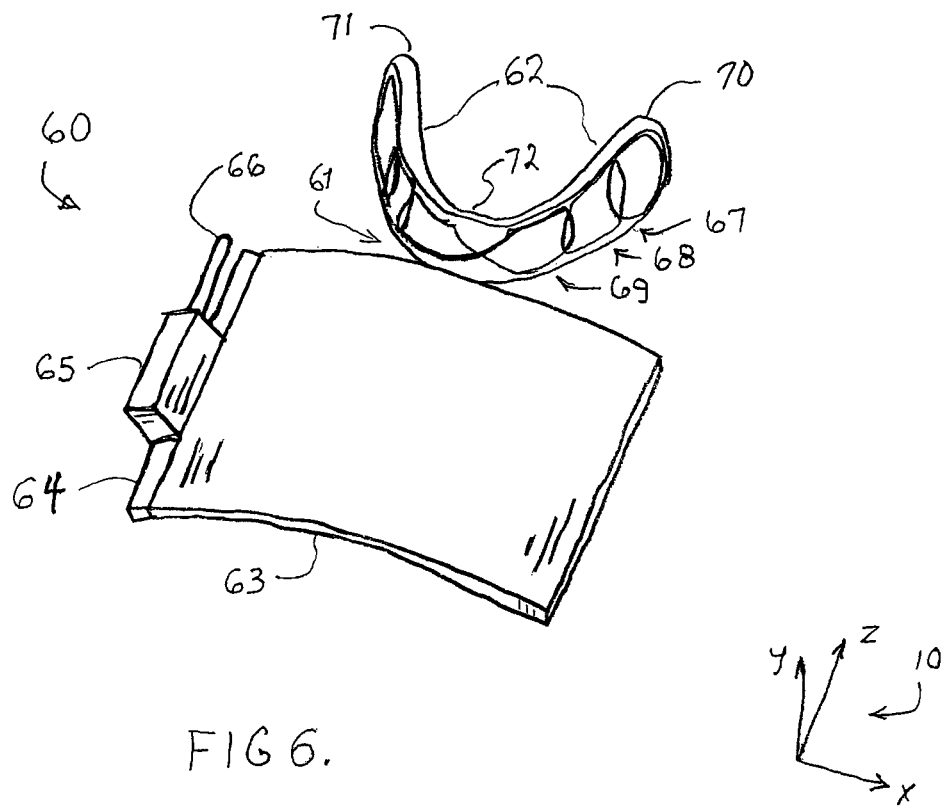
FIG. 6 is a perspective view of a chest and volume neck MRI antenna array in accordance with an alternative embodiment of the present invention.

Referring now to FIG. 6, a flexible, form-fitting chest and volume neck and/or carotid array in accordance with another embodiment of the present invention is shown generally as 60. Array 60 includes a blanket array 63, which is similar or identical to the blanket array 1 shown in FIGS. 1-5B and described above, with stiffeners added to customize the array 63 so that it may be effectively positioned to image the junction 61 of the neck and torso of a person's body. The array 60 includes a plastic reinforced neck section 62, which includes additional antenna elements 67-69, and is joined in hinge fashion to the blanket array 63 with multiple layers of foam and fabric that maintain flexibility at the junction. The neck section 62 is encapsulated in foam in a similar manner as described above with respect to the blanket array 1. The elements (not shown) of the blanket array 63 and elements 67-69 of the neck section 62 include cables (not shown) that are similar to the cables 33 and 52 described above with respect to blanket array 1. Those cables are routed throughout the neck section 62 and blanket array 63 to a side of the blanket array 63 where a hollow plastic cable guide 64 routes and protects the bundle of cables. The cables enter housing 65, which is described above, and cable 66 exits the housing for connection to a MRI system receptacle (not shown) as described above.

Array 60 is one example of optimizing antenna element size and configuration to best match a targeted anatomical region. The blanket array 63 drapes over the anterior chest and covers the clavicles, and neck section 62 is structured to image and wrap around the left and right carotids. The neck section 62 includes antenna elements 67, 68 and 69, the position of which inside of the neck section 62 is represented by the lines drawn in FIG. 6. Elements 67 and 68 are positioned on the left flap 70 of the section 62, and element 69 spans the left and right flaps 70 and 71. There are two additional antenna elements positioned within the right flap 71 of the section 62 that are mirror images of elements 67 and 68 such that the left and right flaps 70 and 71 are mirror images of each other.

Each element 67-69 is sized differently based upon the requisite penetration into the patient to optimize SNR from the carotid arteries. Element 67 is larger than elements 68 and 69 because the elements are farther from the target anatomy of vessels at the superior end of the carotid arteries. Because the curvature 72 of the section 62 around a patient's chin is orthogonal to the Z direction 10, placing a simple loop element at that location would result in no sensitivity to the XY components of the NMR signal (spin). Therefore, element 69 is created as a Helmholtz coil with loop halves on each side of the apex of the curve 72. This creates an element that is sensitive to the X component of spin 10. The array 60 preferably includes a total of either 8 or 16 elements, which includes the five elements within neck section 62. Thus, the blanket array 63 either includes three or eleven elements. The total number of elements is chosen based on compatibility with the MRI system with which the array 60 is used, and the desire to not multiplex signals together from multiple elements to a common signal line or system channel input. However, it is within the scope of the invention to do so based upon clinical design goals. If there are three elements within blanket array 63, they are preferably three quadrature elements sized and spaced within array 63 to have their sensitivity profiles cover the target anatomy (e.g., heart, aorta, carotid origins, and clavicles). If there are eleven elements within blanket array 63, they are preferably eleven single elements.

In an alternative embodiment, the array 60 may include another blanket array 60 that is positioned on the posterior aspect of the patient while the blanket array 60 and neck section 62 shown in FIG. 6 are positioned on the anterior aspect. The cables from the blanket arrays 60 and neck section 62 are preferably routed and combined into one or two common cable assemblies (depending upon MRI system interconnect restrictions) to connect to the MRI system. This further illustrates the convenience of these design building blocks of discrete flexible elements (FIG. 3) built into flexible housings previously described. This assembly is a preferred embodiment of 32 element array with a 16 element posterior blanket coil created such as described above in connection with FIGS. 1-5B combined with the 16 element array 60 of FIG. 6.

The elements of array 60 are preferably positioned and sized to conform to the region of the patient's chest through the lateral clavical regions, the neck and ears to provide continuous coverage of the aortic arteries from their origin laterally through the subclavical arteries and superiorly beyond the superficial temporal arteries.

Figure 7:
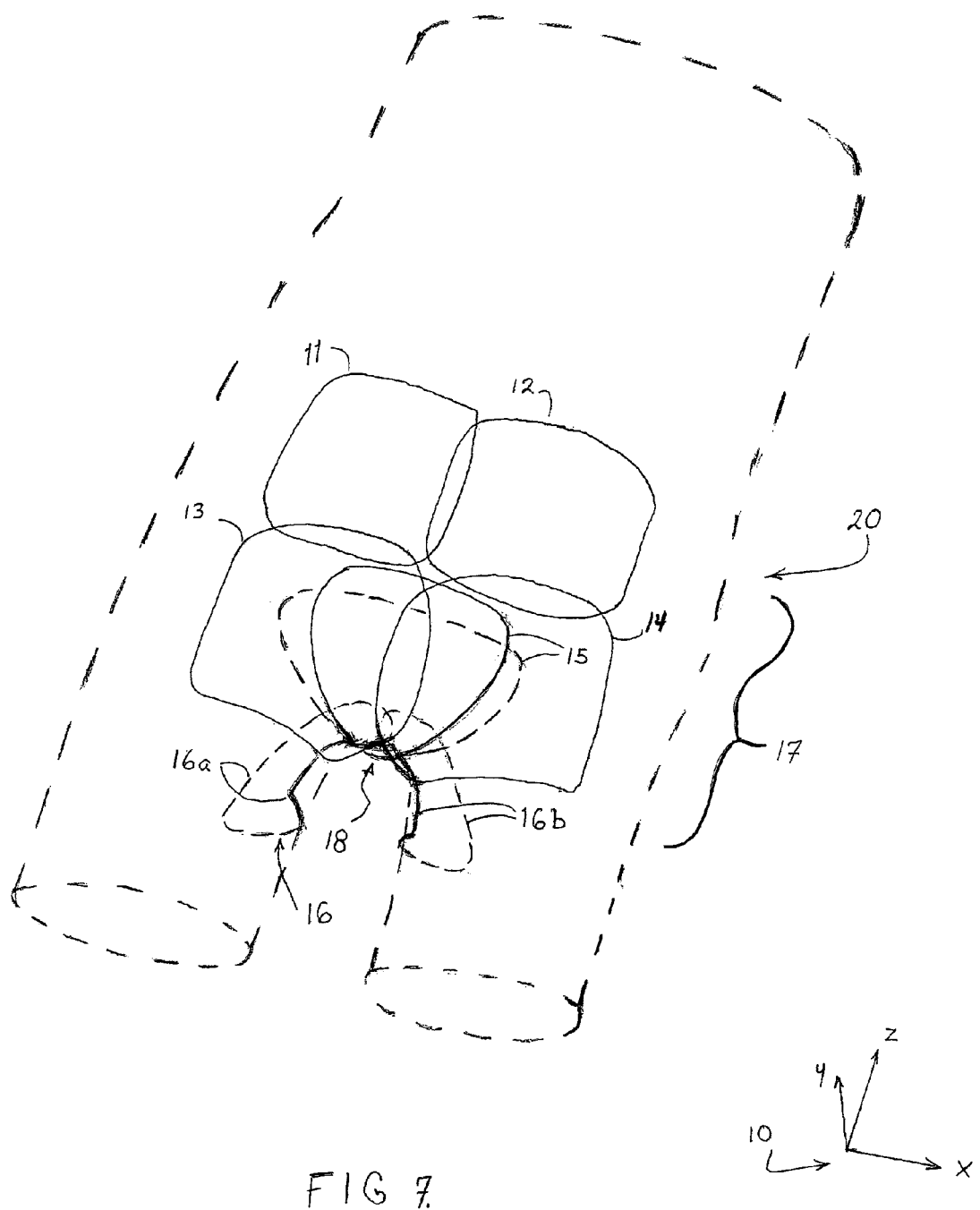
FIG. 7 is a perspective view showing the antenna elements of a pelvic MRI antenna array in accordance with an alternative embodiment of the present invention.

Referring to FIG. 7, a flexible, pelvic MRI antenna array in accordance with another embodiment of the present invention is shown generally as 20. Array 20 is a flexible, wearable garment that is designed to be worn by a person 17 to cover and assist in imaging his/her pelvic region. The array 20 includes flexible and elastic elements 11-16 that are sized and configured for optimal penetration into the target anatomy 17 given the constraints of distance and physical anatomical barriers, such as legs and superficial structures between the various elements 11-16 and the target anatomy of both male and female urological and reproductive organs. The elements 11-16 are mounted on a flexible substrate (not shown) that is similar to substrate 2 described above, but that is formed so that it may be worn like a pair of underwear. The substrate is preferably constructed from an elastic or stretchable material, such as a form of "wet suit," neoprene or similar elastic material. The substrate is elastic or stretchable so that the array 20 is a "one size fits all" array that may be worn by different sized persons. Each element 11-16 is mounted to the substrate in a manner that maintains the flexibility and elasticity of the substrate. The substrate and elements 11-16 are encapsulated by a flexible and elastic housing, such as the housing 1B shown in FIGS. 5A-B, that is preferably constructed from an elastic material such as neoprene and thus does not include the grooves shown in FIGS. 5A-B. The housing may include a layer of foam positioned between the layers of elastic material as described above in order to maintain a consistent thickness at all points of the array 20. The housing and substrate stretches with variations in anatomical size of the different persons wearing the assembly to facilitate the array 20 being pulled on and worn like a garment by various sized and shaped patients during an MRI scan. The housing is sufficiently flexible and elastic to allow the housing to be worn by a plurality of different sized patients so that the housing is in close contact with the patient and conforms to contours of the patient. When the array 20 is worn, each element 11-16 has a unique shape associated with its position relative to the target anatomy and adjacent elements 11-16. These factors affect the 3-D modeling outcome to optimize coverage and penetration of each element's 11-16 sensitivity profile within the patient.

Elements 11 and 12 are the superior, anterior, left and right elements and are larger so that their sensitivity profiles penetrate deeper—as they must due to the increased distance from the inferior torso surface to the target anatomies. These elements 11 and 12 are sensitive to the Y-component of the MRI signal vector due to their orientation generally in the Y plane. Elements 13 and 14 may be single loops such as 11 and 12 and employ critical overlap to ensure mutual inductive null or isolation, with all neighboring elements. Elements 13 and 14 may optionally be capacitively linked together to form a butterfly or Helmholtz coil to create an orthogonal sensitivity profile (X-vector sensitivity), and therefore be intrinsically isolated (aided with some critical overlap as well) from those neighboring elements sensitive to the Y vector. The array 20 may also include in an optional configuration four additional elements (not shown) that mirror elements 11-14 and that are positioned on the posterior side of the patient 17 to provide sensitivity profiles from the opposing patient side as the anterior elements 11-14 shown in FIG. 7. The optional posterior elements (not shown) may be paired as Helmholtz coils in order to keep the total element count at 8, or left as individual elements so that the total element count is 10. The element count is important to consider for economic factors because the array could be designed for use with common 8-channel MRI scanners without extra switching capabilities, or 16 channel scanners. Element 15 is an hour-glass shaped loop with the two ends of the hour glass on the opposing anterior and posterior (shown in dashed lines) sides of the body and connected between the legs. This element 15 exhibits sensitivity to the Y vector throughout the inferior most aspect of the pelvis or torso, the perineum 18. Element 16 consists of two halves 16a and 16b, shown in dashed lines in the posterior region, of a Helmholtz coil lying in a saddle shape against the inner thighs with superior conductors in the region of the perineum 18. This configuration yields a strong local sensitivity to the X-directed vector in the region of the perineum 18.

Figure 8:
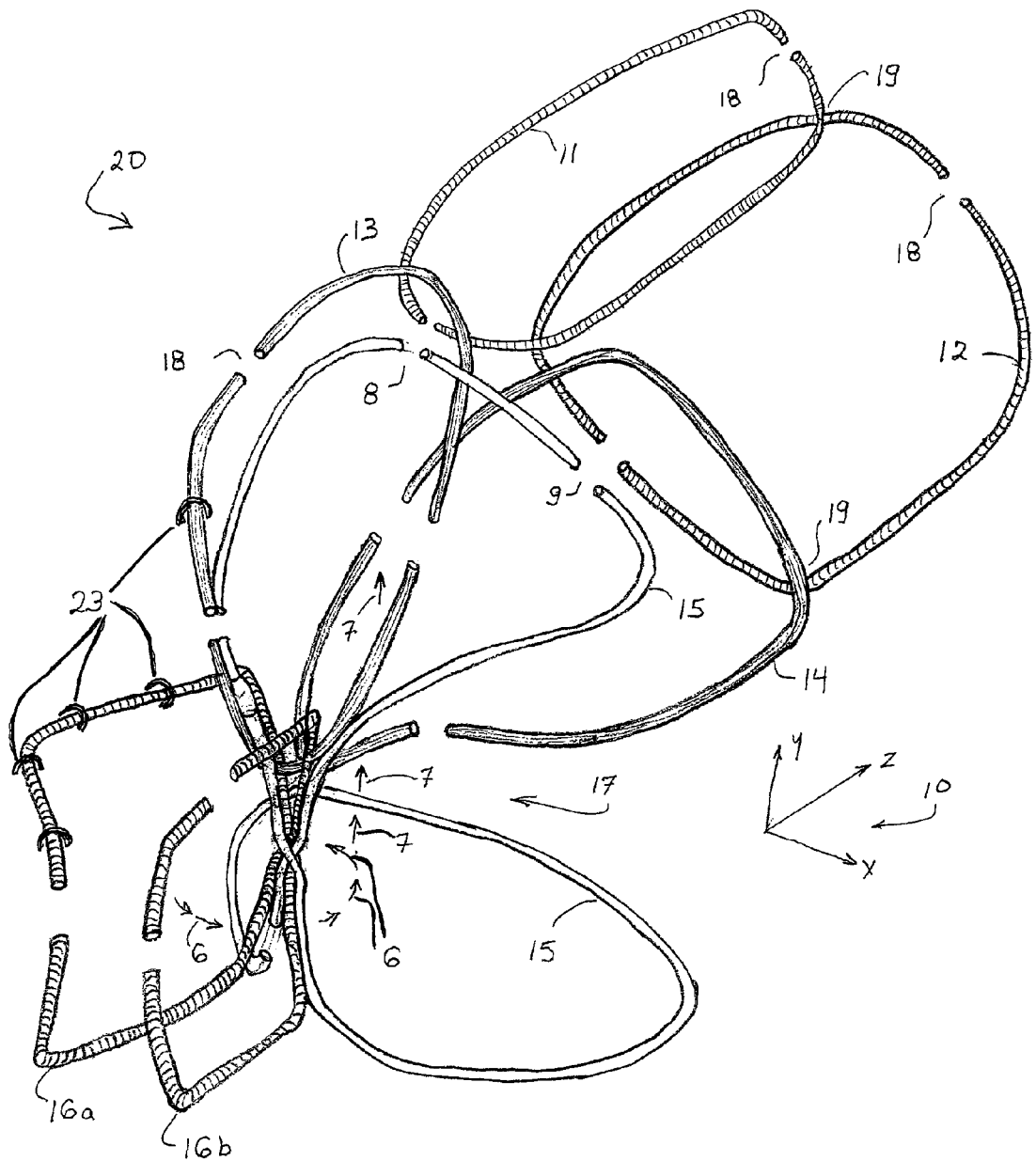
FIG. 8 is a perspective view showing the layout of the antenna elements of the pelvic array shown in FIG. 7 with each antenna element's associated magnetic flux vector indicated.

FIG. 8 illustrates the optimization of element location, size, configuration and spacing in order to create the wearable pelvic garment array 20 shown in FIG. 7. The elements 11-16 of array 20 are joined to a flexible, elastic material (not shown) such as neoprene to create a garment similar to high-waist underwear. The array 20 includes circuit boards and cables (not shown) that are similar to the circuit boards 22, 30, and 40, Baluns 50, and cables 33 and 52 described above in connection with blanket array 1. Elements 11-16 are preferably elastic conductors, such as the elastic conductor 80 described below in connection with FIG. 9, that are joined to a flexible substrate (not shown) of the garment every few centimeters with loose ties 24 that allow the elements 11-16 to flex and move within pre-designed limitations. This allows the elements 11-16 to maintain a desired resonance when the array 60 is worn by a patient and distorted in three dimensions. The elements 11-16 include gaps 8, 9, and 18, which represent where circuit boards 22, 30 and 40 and/or tuning capacitors and isolation inductors are positioned in order to resonate and isolate elements 11-16 from one another. Isolation amongst elements 11-16 is created and maintained, even when the array 60 is distorted in three dimensions, by a combination of non-interfering flux sensitivity profiles (described below), overlaps or gaps 4 (FIG. 10), transformers 5 (FIG. 10), and the isolation preamps discussed previously in connection with FIG. 3. At the regions 19 where the various elements 11-16 cross over one another, the elements may be insulated, or a circuit board may be positioned there, similar to one of the boards 22, 30, or 40, to allow one of the elements to pass under the other as described above in connection with blanket array 1.

Figure 10:
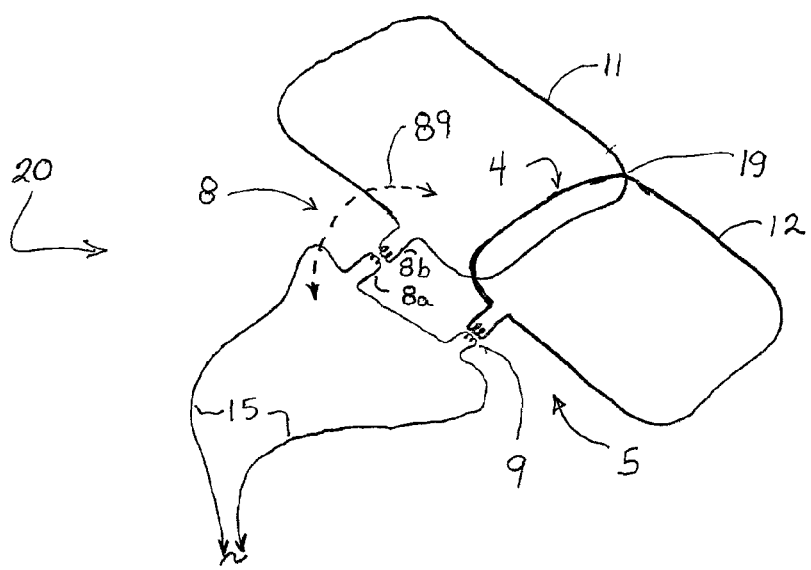
FIG. 10 is a detail view of an isolation transformer network of the pelvic array shown in FIG. 7, which maintains isolation between non-adjacent and/or non-overlapping coil elements.

Element 16 is a Helmholtz coil sensitive to magnetic flux vector X 6 in the target region 17. In the target region 17, element 15 is sensitive to the Y vector 7 and has a sensitivity profile that is modeled to be symmetrical with that of element 16, which intrinsically mutually isolates elements 15 and 16. Elements 13 and 14 are combined into another Helmholtz configuration with sensitivity to the X vector, but are symmetrical and designed to be critically overlapping with the sensitivity profile of neighboring element 16. Elements 11 and 12, which are both sensitive to the Y vector are critically overlapped with each other as well as with pair of elements 13 and 14 to obtain isolation. In many instances, critical overlap is either not possible, due to non-adjacent but nearby element geometries, or due to stray capacitances that exist between nearby elements. In these instances, such as in region 5 (FIG. 10), or in any similar instances whereby elements 11-16 are close enough to sufficiently couple, isolation transformers may be used as shown in FIG. 10 between element 15 and elements 11 and 12. For clarity, FIG. 8 does not show the circuit boards (similar to boards and Baluns 22, 30, 40 and 50), cables (similar to cables 33 and 52), elastic bands of the garment that represent the top waist of the garment, and plastic housing (similar to housing 65) that also form a part of the array 20. The cables (similar to cables 33 and 52) preferably form a bundle of cables (similar to bundle 47) at the posterior, lateral side of the array 20. A housing (similar to housing 65) is preferably attached to the outside of the garment with multiple plastic rivets. FIG. 8 also does not show for clarity the optional posterior elements previously discussed which may mirror anterior elements 11-14.

FIG. 9 shows one type of elastic or stretchable conductor 80 that may be used to form any of the elements 11-16 of array 20, any of the elements 21 of array 1, any of the elements of array 60, or any of the elements of array 90 described below. The conductor 80 may also be used for any of the cables 33 and 52 for any of the arrays 1, 20, 60, or 90 described herein. The conductor 80 includes an elongate, hollow, cylindrical tight weave mesh 81 of fine conducting wires that are similar to the outer shielding of a flexible coaxial cable. Conductor 80 includes an inner insulator 82, which is an elongate, hollow, cylindrical elastic band positioned inside of the mesh 81. The inner insulator 82 replaces the non-elastic insulator of a typical coaxial cable. The insulator 82 has an outer diameter that is approximately equal to the inner diameter 83 of mesh 81 where it is stretched out or not bunched together. The insulator 82 assists in maintaining a more constant shape of the conductor 80 as it expands and contracts within the confines of its attachment points 23 and 84. Attachment points 23 are accomplished with guide clamps 24 similar to eyelets that allow the conductor 80 to slide and stretch in a controlled manner through the opening of the clamp 24. Eyelet/clamp 24 is affixed to the flexible substrate (not shown) by sewing or rivet through premade holes 88 in the clamp 24. Attachment points 84 are provided by the physical soldering of conductor assembly 80 to boards 30, 40 or 22, as discussed above with respect to attachment points 27*a-m* shown in FIG. 3, and encapsulated by the strain reliefs 26 aforementioned. Expansion and contraction of conductor 80 is facilitated by predetermined bunching of the wire mesh 81 at strategic locations or bulges 85, and further aided and controlled by the inner insulator 82. The inner conductor 8 that exists in conventional coaxial cable is removed in this rendition as it is inflexible, although its typical location is shown in FIG. 9. If a replacement conductor is desirable for carrying the aforementioned decoupling currents, then a highly flexible, insulated, multi-strand wire 86 is threaded through the mesh 81 and allowed to bunch within the bulge 85; thus enabling flexibility and expansion of both conductors, wire mesh 81 and wire 86. Expansion and contraction of bulges 85 only nominally affects the inductance and frequency tuning of the conductor 80 due to the construction of wire mesh 81. A signal traveling through the wire mesh 81 must travel approximately the same distance through a bulge 85 whether it is contracted as shown in FIG. 9 or expanded when the conductor 80 is under tension. Because the distance is approximately the same, inductance and frequency tuning of the conductor 80 are only affected nominally. As an array containing the conductor 80 is worn by a patient and stretched, the bulges 85 expand as necessary, which permits the array to be worn by a patient of virtually any size. The substrate to which the conductor is attached via clamps 24, such as substrate 2 described above, is preferably elastic and has a memory that causes the bulges 85 to contract back to their original shape when the array is no longer worn by a patient and being stretched.

Referring then to FIG. 10, the anterior elements 11 and 12 of the pelvic array 20 are positioned near, but not overlapping the anterior aspect 5 of element 15. Therefore, isolation may be improved between these elements 11, 12, and 15 by employing transformers 8 and 9. RF currents flowing in element 11 pass through a winding 8*b* of transformer 8 while RF currents flowing in element 15 pass through a winding 8*a*. Windings 8*a* and 8*b* are wound in opposite directions and coupled such that their mutual inductance exactly equals the mutual inductance 89 of the two loops 11 and 15; hence, the total mutual coupling between the two elements 11 and 15 is nullified. Transformer 9 is similarly employed with elements 12 and 15. Elements 11 and 12 require no transformer due to the critical overlap 4.

Figure 11:
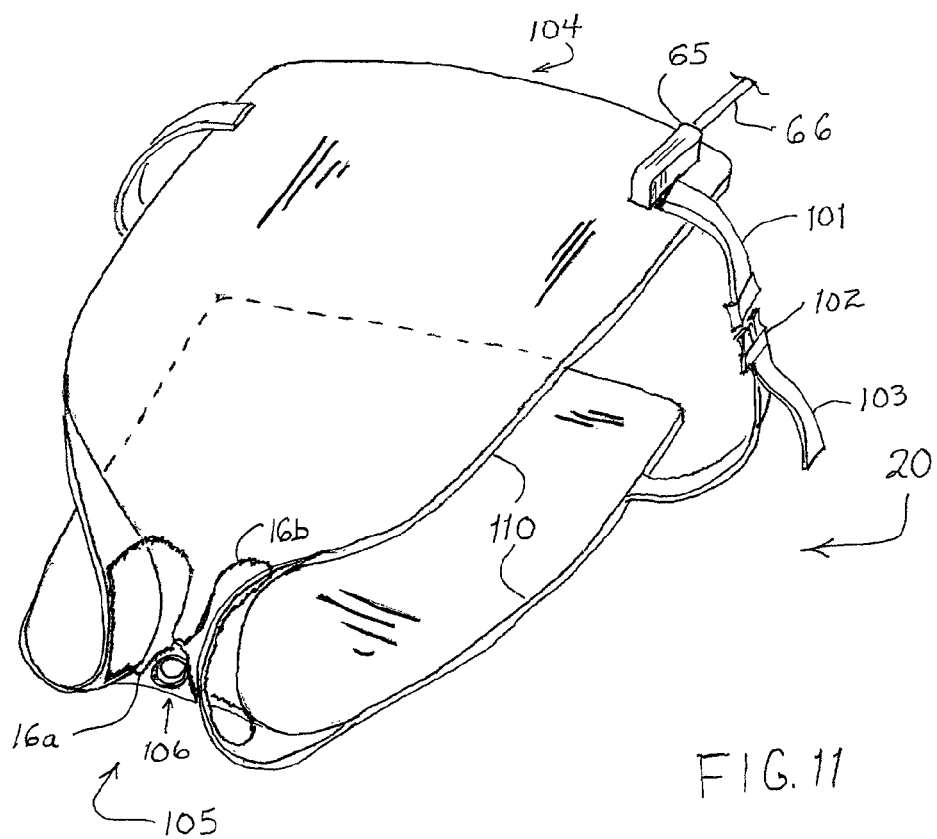
FIG. 11 is a perspective view of a pelvic array to which the antenna elements shown in FIG. 7 are mounted.

Referring now to FIG. 11, a preferred garment forming a part of and incorporating the pelvic coil array 20 shown in FIGS. 7 and 8. The garment is a diaper-like foam housing 110 that encapsulates the elements 11-16 and associated circuit boards and cables. The housing 110 has an adjustable latching mechanism including web belts 101 terminated with a pair of mating plastic clips 102. The belts 101 have an adjustable strap length 103 to firmly attach the garment 110 generally just above a plurality of different sized patients' waists 104. The belts 101 and clips 102 are duplicated on each side of the housing 110. The garment also includes a cable housing 65, as described above, which receives the cables from the elements and their associated circuit boards. The cable housing 65 insulates and protects the cable bundle and houses a mating connector (not shown) that allows for a quick disconnect of the system cable 66 from the housing 65, which makes it convenient to strap on the garment 110 in a dressing room before the patient is positioned on the scanning table and system cable 66 is connected to housing 65.

FIG. 11 also shows a superposition of the flexible elements 16*a-b* contained within the foam housing 110 with a variation of their location to accommodate an opening 105 in the foam housing 110 and substrates in the region of a patient's anus. An alternative location for the opening 105 would be in the region of a patient's vaginal canal. This optional configuration of the design would include a rubber (or similar plastic material) grommet 106 which seals the many layers of substrate and foam on the inside of the opening 105 diameter with lips around the opening 105 on both sides (patient side and outside) of the housing 110. The grommet 106 maintains a generally cylindrical canal opening to provide access to either the rectum and prostate glands or vaginal canal. This is to facilitate the insertion of endocavitary probes or biopsy needles to access suspect tissues while co-registering location using MRI.

Figure 12:
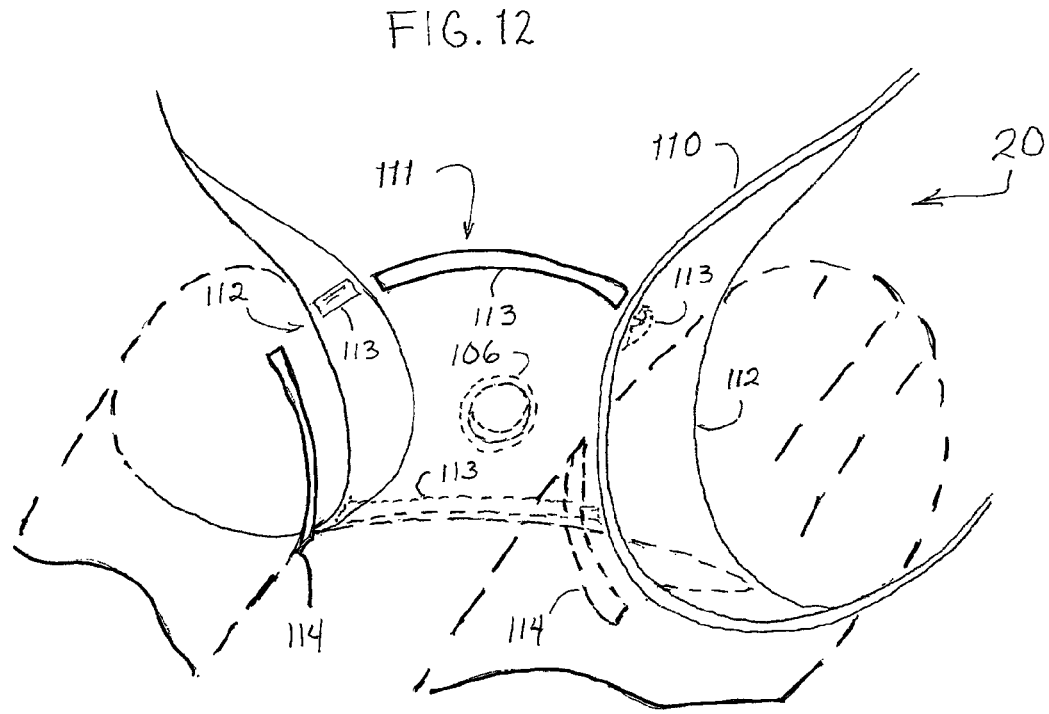
FIG. 12 is a close-up detail view of one embodiment of a disposable patient liner for use with the pelvic array shown in FIG. 11.

FIG. 12 further illustrates detail of the diaper-like pelvic housing 110 and the use and attachment of a disposable liner 111 which lines the entirety of the inner or patient contact surface 112 and protrudes through the access grommet 106 similar to a funnel from the inside. The flexible plastic liner 111 then flairs out again after tunneling through the grommet 106 and temporarily attaches to the outer surfaces of the housing 110 at adhesive strips 113 well away from the opening 105 on the anterior, posterior and lateral surfaces of the housing 110. The liner 111 also attaches to the patient's inner thighs at adhesive strip locations 114. After the insertion procedure, scanning is accomplished, and the probes are removed, the surface of the external portion of the liner 111 is wiped. Then, the liner 111 is unstuck from the adhesive locations and bunched into a tight bundle protruding from the grommet 106. The housing 110 is then removed from the patient, and the liner 111 is withdrawn from grommet 106 from the inside and discarded. This procedure keeps the surfaces of the housing 110 clean of biological contaminant.

Figure 13:
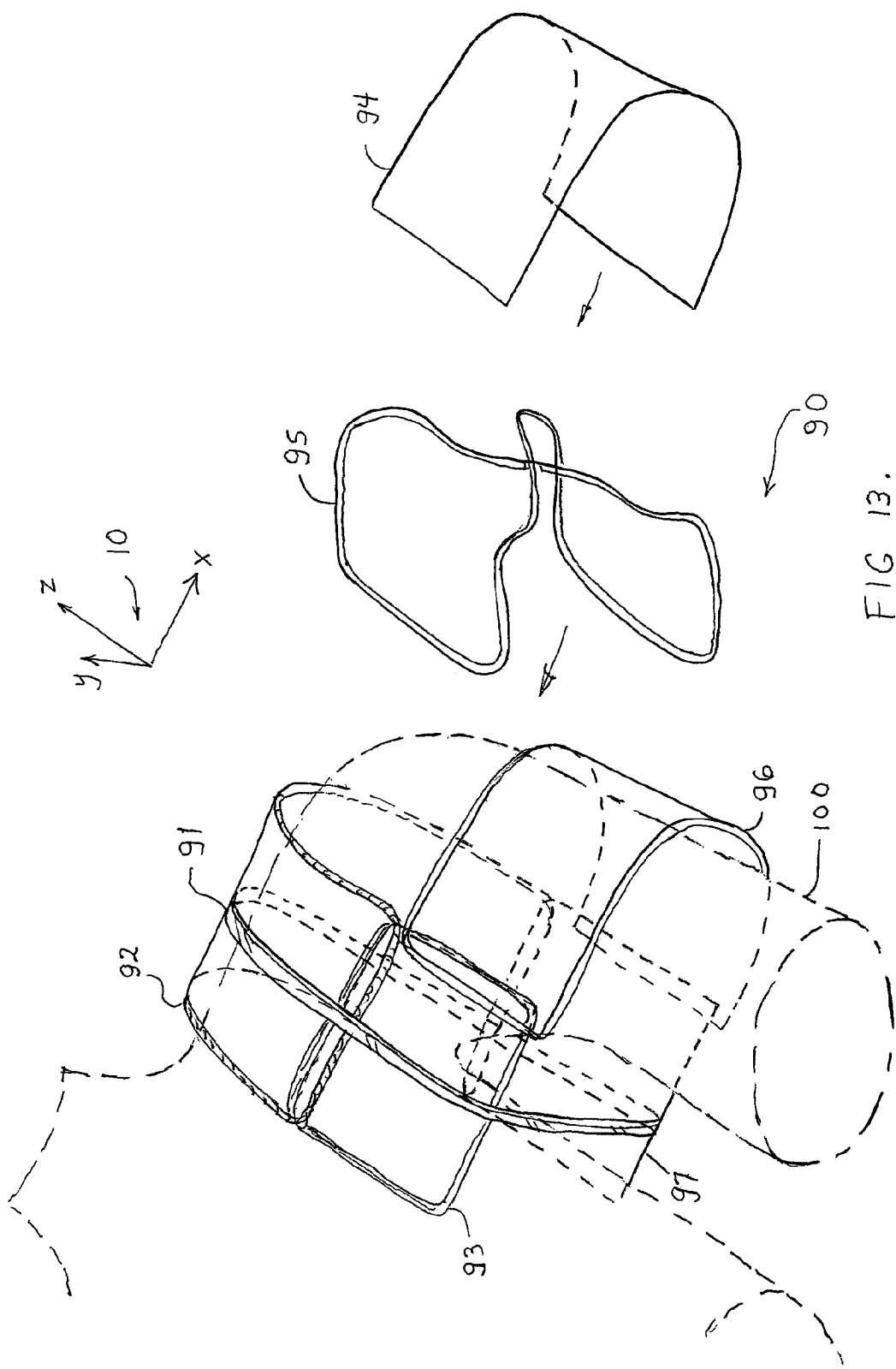
FIG. 13 is a perspective view of a shoulder MRI antenna array in accordance with an alternative embodiment of the present invention.

Referring now to FIG. 13, a seven element flexible, wearable shoulder antenna array in accordance with another alternative embodiment of the present invention is shown generally as 90. The array 90 further illustrates the solution of selecting variations in element geometry, configurations, size and isolation mechanisms in order to obtain more signal from a given common volume—the shoulder joint and surrounding anatomy of subject 100. Elements 91-97 are shown in FIG. 13 in a similar manner as elements 11-16 are shown in FIG. 8. While the elements 91-97 are shown without gaps, they preferably have gaps where they are joined with circuit boards (similar to boards and Baluns 22, 30, 40, and 50). Circuitry on the circuit boards is electrically coupled with the elements 91-97 for maintaining tuning and isolation between the elements when the housing is worn by a patient and distorted in three dimensions. The array 90 also includes cables (similar to cables 33 and 52) and a plastic housing (similar to housing 65) where the cables terminate.

Element 91 is a solenoidal coil that slips under the armpit and over the collar bone such that it is oriented and sensitive to the X vector MRI signal. Solenoid 91 bisects the superior Helmholtz 92 which is sensitive to the Y vector and therefore geometrically isolated. Elements 93 and 97 are single loop elements also bisected by element 91 and are both sensitive to the Y component and also geometrically isolated from 91. Elements 94 and 96 are the superior and inferior saddle coils which fit over the outside (lateral aspect) of the arm and shoulder and are sensitive to the X component, critically overlapped with each other for isolation and also with elements 93, 97 and 91 for isolation. Their distance from element 91 creates nominal coupling with 91 and are therefore operable as is; however, different sized coil assemblies may require isolation transformers between these elements as previously discussed and shown in FIG. 10. Finally, element 95 is an Helmholtz saddle coil configuration which bisects elements 94 and 96 and is geometrically decoupled with its symmetry and orthogonal sensitivity profile to the two. Elements 94 and 95 are shown moved away from the actual position about the shoulder for clarity. All elements 91-97 are fastened to a stretchable material, in a similar manner as previously discussed above with respect to the pelvic array 20, and are allowed to flex sufficiently to facilitate pulling the garment over the shoulder. Specifically, the elements 91-97 are mounted to a flexible and elastic substrate, similar to substrate 2 described above. The elements 91-97 are attached to the substrate with clamps, similar to clamps 24 described above, that permit the elements 91-97 to maintain a desired resonance when the array 90 is worn and distorted in three dimensions. The substrate and elements 91-97 are encapsulated by a flexible and elastic housing, such as the housing 1B shown in FIGS. 5A-B, that is preferably constructed from an elastic material such as neoprene and thus does not include the grooves shown in FIGS. 5A-B. The housing is sufficiently flexible and elastic to allow it to be worn by a plurality of different sized patients so that the housing is in close contact with the patient and conforms to the contours of the patient. The housing may include a layer of foam positioned between the layers of elastic material as described above in order to maintain a consistent thickness at all points of the array 20. The elements 91-97 are preferably constructed in the same manner as flexible and elastic conductor 80, shown in FIG. 9, so that they are able to sufficiently flex and stretch when the garment is worn by patients of different sizes. Further, the components of array 90 are preferably sufficiently flexible and elastic to permit a patient to extend his/her arm out to the side of the patient's body and above the patient's head.

Other types of MRI antenna arrays are within the scope of the present invention besides the blanket array 1, chest and volume neck array 60, pelvic array 20, and shoulder array 90. The manner in which these arrays are constructed to make them flexible and/or elastic may be used to form an array designed to be placed over any body part or worn by a patient for placement over any body part in such a manner that the array is in close contact with the patient and closely conforms to contours of the patient. By way of example, it is possible and within the scope of the present invention to produce a full body suit using the same techniques as described above that may be worn by a patient to image most or all areas of the patient. Antenna arrays with more than the specific number of antenna elements described with respect to any of the embodiments above are also within the scope of the present invention. For example, in a full body suit MRI garment, any number of antenna elements may be used in order to sufficiently image the patient.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A magnetic resonance imaging antenna array for detecting nuclear magnetic resonance signals from a patient, comprising:
a flexible substrate;
at least one rigid board coupled to the flexible substrate;

a first antenna element coupled to both the flexible substrate and the rigid board, wherein the first antenna element is flexible; and a second antenna element coupled to both the flexible substrate and the rigid board, wherein the second antenna element is flexible, wherein a portion of the first antenna element overlaps a portion of the second antenna element in a location that is adjacent to both where the first antenna element is coupled to the rigid board and where the second antenna element is coupled to the rigid board, and wherein an area is circumscribed by the first and second antenna elements.

2. The array of claim 1, wherein at least one of the first and second antenna elements is coupled to said substrate with at least one clamp that permits the at least one of the first and second antenna elements to move a desired amount through said clamp.

3. The array of claim 1, further comprising a second rigid board coupled to the flexible substrate, wherein the first antenna element is coupled to the second rigid board, wherein the second antenna element is coupled to the second rigid board, wherein a portion of the first antenna element overlaps a portion of the second antenna element in a location that is adjacent to both where the first antenna element is coupled to the second rigid board and where the second antenna element is coupled to the second rigid board.

4. The array of claim 1, wherein the area circumscribed by the first and second antenna elements remains constant as the substrate is distorted in three dimensions in order to maintain inductive isolation between the first and second antenna elements.

5. The array of claim 1, further comprising a housing that at least partially encapsulates the flexible substrate, rigid board, first antenna element, and second antenna element, wherein said housing, substrate, rigid board, and first and second antenna elements form a blanket which is able to flex in three dimensions.

6. The array of claim 5, wherein said housing, substrate, rigid board, and first and second antenna elements are formed from relatively small, lightweight materials so that said blanket may be draped over an infant patient in a manner that does not compromise the patient's breathing.

7. The array of claim 1, further comprising a housing that at least partially encapsulates the flexible substrate, rigid board, first antenna element, and second antenna element, wherein said housing, substrate, rigid board, and first and second antenna elements are configured to be positioned over the patient's torso and a portion of the patient's neck.

8. The array of claim 7, further comprising a plurality of antenna elements configured as a carotid array.

9. The array of claim 8, wherein the housing comprises a generally planar blanket joined to an arcuate neck section, wherein the first and second antenna elements are encapsulated by the blanket and the carotid array is encapsulated by the arcuate neck section.

10. The array of claim 5, wherein said housing comprises a plurality of grooves and non-grooved regions separated by said grooves.

11. A magnetic resonance imaging antenna array for detecting nuclear magnetic resonance signals from a patient, comprising:
a flexible housing comprising at least one non-grooved region having a first thickness and at least one grooved region having a second thickness, wherein the second thickness is less than the first thickness when the housing is positioned so that it is generally planar;
a flexible substrate at least partially encapsulated by said housing; and
a plurality of antenna elements coupled to the substrate and at least partially encapsulated by said housing.

12. The array of claim 11, further comprising a cable that is electrically coupled with at least one of the antenna elements, and a hollow cable guide attached to said housing and receiving a portion of said cable.

13. The array of claim 11, where the housing comprises compressible foam.

14. The array of claim 11, further comprising a circuit board coupled to at least one of the plurality of antenna elements, wherein the non-grooved region comprises a hollowed out or thinner area that covers the circuit board.

15. The array of claim 5, wherein the housing comprises:
flat sheets that encapsulate the flexible substrate, rigid board, first antenna element, and second antenna element; and
foam positioned between the sheets, wherein the foam comprises a cut out or compressed region that is aligned with the rigid board such that the housing has a relatively constant thickness.

* * * * *